(12) United States Patent
Sakai et al.

(10) Patent No.: US 8,190,378 B2
(45) Date of Patent: May 29, 2012

(54) CRACK GROWTH EVALUATION APPARATUS, CRACK GROWTH EVALUATION METHOD, AND RECORDING MEDIUM RECORDING CRACK GROWTH EVALUATION PROGRAM

(75) Inventors: Hidehisa Sakai, Kawasaki (JP); Katsufumi Morimune, Hyogo (JP); Masanori Motegi, Kawasaki (JP); Tsutomu Iikawa, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 28 days.

(21) Appl. No.: 12/289,616

(22) Filed: Oct. 30, 2008

(65) Prior Publication Data
US 2009/0187353 A1    Jul. 23, 2009

(30) Foreign Application Priority Data
Jan. 23, 2008  (JP) .................................. 2008-12272

(51) Int. Cl.
*G01B 5/28* (2006.01)
(52) U.S. Cl. ................ 702/35; 702/33; 702/34; 702/42; 702/81; 702/79; 702/193; 702/132; 73/799
(58) Field of Classification Search ...................... 702/35
See application file for complete search history.

(56) References Cited

U.S. PATENT DOCUMENTS

| | | | |
|---|---|---|---|
| 5,455,777 A | 10/1995 | Fujiyama et al. | |
| 5,826,213 A | 10/1998 | Kennefick | |
| 6,006,163 A | 12/1999 | Lichtenwalner et al. | |
| 7,454,297 B2 * | 11/2008 | Balestra | ........................ 702/42 |
| 7,480,601 B2 | 1/2009 | Tyron, III | |
| 7,831,396 B2 * | 11/2010 | Voigtlaender et al. | .......... 702/34 |
| 7,889,840 B2 * | 2/2011 | Vasudevan et al. | ............. 378/58 |
| 2001/0047691 A1 | 12/2001 | Dzenis | |
| 2004/0031337 A1 | 2/2004 | Masaniello et al. | |
| 2004/0148143 A1 | 7/2004 | Deobald et al. | |
| 2004/0158450 A1 | 8/2004 | Nakadate et al. | |
| 2004/0225474 A1 | 11/2004 | Goldfine et al. | |

(Continued)

FOREIGN PATENT DOCUMENTS

JP          2004-79914          3/2004

(Continued)

OTHER PUBLICATIONS

Blish et al, "Semiconductor Device Reliability Failure Models," 2000, International Sematech.*

(Continued)

*Primary Examiner* — Drew A Dunn
*Assistant Examiner* — Hyun Park
(74) *Attorney, Agent, or Firm* — Staas & Halsey LLP

(57) ABSTRACT

An element damage determination unit calculates a cumulative value of a damage value using a Manson-Coffin law for a plurality of finite elements of a continuum based on a result of a stress/distortion analyzing process, and determines whether or not the cumulative value of the damage value is equal to or exceeds a threshold. A calculation unit obtains first correspondence information indicating the correspondence between the number of cycles of a load and a growth rate of a crack occurring in the continuum based on the determination result. A Manson-Coffin law change unit changes a Manson-Coffin law based on the first correspondence information and second correspondence information indicating the correspondence between an actual measurement value of the number of cycles of a load applied to the continuum and an actual measurement value of the growth rate of a crack occurring in the continuum at that time.

8 Claims, 19 Drawing Sheets

U.S. PATENT DOCUMENTS

| | | |
|---|---|---|
| 2005/0200243 A1 | 9/2005 | Spangler et al. |
| 2006/0009837 A1 | 1/2006 | Burgermeister et al. |
| 2006/0089823 A1 | 4/2006 | Meyer et al. |
| 2006/0206295 A1 | 9/2006 | Tyron, III |

FOREIGN PATENT DOCUMENTS

| | | |
|---|---|---|
| JP | 2004-237304 | 8/2004 |
| JP | 2004-045343 | 12/2004 |
| JP | 2006-071406 | 3/2006 |
| JP | 2006-71406 | 3/2006 |
| JP | 3900042 | 1/2007 |

OTHER PUBLICATIONS

Sawada, JP2004-054863 (English Abstract only).*

Rots, "Removal of finite elements in strain-softening analysis of tensile fracture," Fracture mechanics of concrete structures, ed, Bazant (1992) in digital form 2005.*

Simonovski et al., "The influence of crystallographic orientation on crack tip displacements of microstructurally small, kinked crack crossing the grain boundary", Computation Materials Science, 2006; pp. 817-828.

Harte et al., "On progressive damage phenomena of structures", Computational Mechanics, 2000; pp. 404-412.

Mohr, W, "Strain based design of pipelines", U.S. Department of Interior, Minerals and management Service, 2003; 137 pages.

U.S. Office Action for related U.S. Appl. No. 11/984,310; mailed Jun. 1, 2010.

U.S. Notice of Allowance for related U.S. Appl. No. 11/984,310; mailed Feb. 16, 2011.

* cited by examiner

| CONTINUUM | GROWTH PATH OF CRACK |
|---|---|
| A | 1→2→3→4 |
| B | 10→11→12 |
| ⋮ | ⋮ |

| NODE NUMBER | COORDINATES |
|---|---|
| 1 | (a, b, c) |
| 2 | (d, e, f) |
| ⋮ | ⋮ |

| FINITE ELEMENT | NODE NUMBER | CUMULATIVE DAMAGE VALUE D | DETERMINATION RESULT |
|---|---|---|---|
| AA | 1 | ppp | 1 |
| BB | 2 | qqq | 0 |
| ⋮ | ⋮ | ⋮ | ⋮ |

21 though the present invention relates to a crack growth evaluation

CRACK GROWTH EVALUATION APPARATUS, CRACK GROWTH EVALUATION METHOD, AND RECORDING MEDIUM RECORDING CRACK GROWTH EVALUATION PROGRAM

CROSS-REFERENCE TO RELATED APPLICATIONS

This application claims the conventional priority based on Japanese Application No. 2008-012272, filed on Jan. 23, 2008, the disclosures of which are incorporated herein by reference.

BACKGROUND OF THE INVENTION

1. Field of the Invention

The present invention relates to a crack growth evaluation apparatus, a crack growth evaluation method, and a recording medium recording a crack growth evaluation program. More specifically, the present invention relate to a crack growth evaluation apparatus, a crack growth evaluation method, and a recording medium recording a crack growth evaluation program capable of evaluating with high accuracy the growth of a crack occurring in a continuum in a finite element method.

2. Description of the Related Art

For a solder material and various types of joining resin material (adhesive), stable connection reliability of a junction is important. Practically, it is necessary for a connected portion to have sufficient durability in the temperature cycle and the mechanical cycle of oscillations and so on cyclically applied in an actual use environment. In the designing stage of a connected portion, there is a method for calculating a stress and a distortion by performing a simulation using a finite element method and so on, and indirectly evaluating the life and so on based on the calculated stress and distortion values. The method has been conventionally used in many parts and device development evaluations. Especially, in estimating the count of the cyclic fatigue life such as temperature cyclic fatigue, a method for estimating the cyclic fatigue life count using a Manson-Coffin law based on a distortion value obtained from a simulation result using the finite element method and so on.

FIG. 25 is a diagram showing an analysis model of a soldered portion. An analysis model of a soldered portion 102 is used in a simulation performed in the finite element method and so on. In a conventional method, the following equation 1 calculates $N_f$ as the count of cyclic fatigue life in the Manson-Coffin law by obtaining a distortion amplitude value $\Delta\epsilon_{in}$ for the finite element of the portion enclosed by the circle in bold type using the analysis model.

$$N_f = 1/2 \cdot (\Delta\epsilon_{in}/\epsilon_o)^{-n} \quad \text{(equation 1)}$$

In the equation 1, n and $\epsilon_0$ are parameters depending on the material and shape of the soldered portion 102.

Proposed is a system of calculating an amount of distortion occurring at a soldered portion in electronic equipment configured by a wiring substrate whose opposing surfaces have electronic parts attached through a soldered portion by inputting optional position related information among electronic parts to a stress curve displayed with an amount of distortion occurring at a soldered portion being associated with position related information among electronic parts (refer to the Japanese Patent No. 3900042).

The conventional technique for calculating the count of cyclic fatigue life $N_f$ based on the finite element method and the Manson-Coffin law (hereinafter referred to simply as conventional technique) evaluates a life using stress and distortion occurring at a soldered portion having an initial shape. Therefore, when a crack occurs in a soldered portion, the count of cyclic fatigue life can be estimated.

However, in the conventional technique, since an initial shape (produced shape) is used as the shape of an analysis model of a soldered portion, it is difficult to assume the state of a stress when a crack develops in the soldered portion. In addition, several hundreds to several tens of thousands cycles are repeated in a temperature cycle and a mechanical cycle test. However, a current computer requires several hours to several days to complete a one cycle process. Therefore, it requires quite a long time and is not practical for a computer to iteratively execute several hundreds cycles. Accordingly, with the conventional technique, it is practically difficult to estimate a complete fracture life until the final fracture after the growth of a crack in the soldered portion and to estimate the growth process of a crack.

In addition, if a simulation result is different from an actual measurement result when a growth process of a crack occurring in a continuum such as a soldered portion and so on is simulated in the conventional technique, the simulation result is not corrected based on the actual measurement result.

Furthermore, in the conventional technique, when a growth rate of a crack occurring in a continuum is obtained based on a simulation result of a growth process of a crack occurring in the continuum, the growth rate of a crack cannot be automatically obtained. Therefore, it is necessary to temporarily display the data indicating the crack (for example, data of a cumulative damage value of finite elements obtained by dividing a continuum) on a display screen, and actually measure the length of the crack on the display screen. Accordingly, the growth of a crack occurring in a continuum cannot be accurately evaluated in the conventional technique.

SUMMARY OF THE INVENTION

It is an object of the present invention to provide a crack growth evaluation apparatus that accurately evaluates the growth of a crack occurring in a continuum.

It is another object of the present invention to provide a crack growth evaluation method for accurately evaluating the growth of a crack occurring in a continuum.

It is still another object of the present invention to provide a recording medium recording a crack growth evaluation program for accurately evaluating the growth of a crack occurring in a continuum.

The crack growth evaluation apparatus is a crack growth evaluation apparatus that evaluates a growth of a crack occurring in a continuum. The crack growth evaluation apparatus comprises a generation unit generating an analysis model used in analyzing stress and distortion occurring in the continuum by a finite element method and obtained by dividing the continuum into a plurality of finite elements, an analysis unit analyzing, by the finite element method, a stress and a distortion occurring by a load cyclically applied to the continuum in each of a plurality of finite elements of the continuum for each cycle of the load using the analysis model, a determination unit calculating a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold, a calculation unit calculating a growth rate of a crack occurring in the continuum when the cycle of the load terminates for each cycle of the load based on the determination result by the determination unit, and obtaining first correspondence information indicating a correspondence between the number of cycles of a load and the growth rate of a crack, and a Manson-Coffin law change unit changing the Manson-Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum.

Preferably, the crack growth evaluation apparatus further comprises a change unit deleting a finite element having a cumulative value of the damage value equal to or exceeding the threshold when the cumulative value is equal to or exceeds the threshold, or changing rigidity of the finite element. The analysis unit analyzes stress and distortion occurring by a load of a next cycle after a current cycle for each of a plurality of finite elements of the continuum whose finite element is deleted or whose rigidity is changed by the change unit when the current cycle of the load cycle terminates.

Preferably, the calculation unit sets a node arranged at a starting position of the growth path of the crack where the cumulative value is equal to or exceeds the threshold as the node where a crack starts using extrapolated information stored in advance in a storage unit, calculates a path length from the node where a crack starts to a last node where the cumulative value is equal to or exceeds the threshold as a length of the crack occurring in the continuum, and calculates a rate of the calculated crack length to a total length of the growth path of a crack as a growth rate of a crack occurring in the continuum. The Manson-Coffin law change unit obtains an actual measurement value of the number of cycles of a load when the growth rate of a crack calculated by the calculation unit and the number of cycles of a load corresponding to the growth rate of a crack respectively match an actual measurement value of the growth rate of a crack and an actual measurement value of the number of cycles of a load corresponding to the actual measurement value of the growth rate of a crack, calculates a nonlinear distortion amplitude value corresponding to the obtained actual measurement value of the number of cycles of a load based on the Manson-Coffin law, and obtains a new Manson-Coffin law based on the calculated nonlinear distortion amplitude value and the obtained actual measurement value of the number of cycles of a load.

Preferably, the crack growth evaluation apparatus further comprises a display unit displaying a state of a growth of a crack occurring in the continuum using the analysis model based on a determination result by the determination unit.

The crack growth evaluation method is a crack growth evaluation method for evaluating a growth of a crack occurring in a continuum. The crack growth evaluation method comprises generating an analysis model used in analyzing stress and distortion occurring in the continuum by a finite element method and obtained by dividing the continuum into a plurality of finite elements, analyzing, by the finite element method, a stress and the distortion occurring by a load cyclically applied to the continuum in each of a plurality of finite elements of the continuum for each cycle of the load using the analysis model, calculating a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold, calculating a growth rate of a crack occurring in the continuum when the cycle of the load terminates for each cycle of the load based on the determination result, and obtaining first correspondence information indicating a correspondence between the number of cycles of a load and the growth rate of a crack, and changing the Manson-Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum.

The recording medium recording a crack growth evaluation program is a computer-readable recording medium recording a crack growth evaluation program for evaluating a growth of a crack occurring in a continuum. The program causes a computer to execute generating an analysis model used in analyzing stress and distortion occurring in the continuum by a finite element method and obtained by dividing the continuum into a plurality of finite elements, analyzing, by the finite element method, a stress and the distortion occurring by a load cyclically applied to the continuum in each of a plurality of finite elements of the continuum for each cycle of the load using the analysis model, calculating a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold, calculating a growth rate of a crack occurring in the continuum when the cycle of the load terminates for each cycle of the load based on the determination result, and obtaining first correspondence information indicating a correspondence between the number of cycles of a load and the growth rate of a crack, and changing the Manson- Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum.

The crack growth evaluation apparatus, the crack growth evaluation method, and the recording medium recording a crack growth evaluation program calculate the cumulative value of the damage value using a Manson-Coffin law on each of a plurality of finite elements of a continuum based on a result of a stress and distortion analysis using an analysis model of a continuum, determine whether or not the cumulative value of the damage value is equal to or exceeds a threshold, and change the Manson-Coffin law according to the first correspondence information obtained based on the determination indicating the correspondence between the number of cycles of a load and the growth rate of a crack occurring in the continuum and the second correspondence information obtained based on an actual measurement value. That is, based on the result of the simulation of the growth process of a crack occurring in a continuum (first correspondence information indicating the correspondence between the number of cycles and the growth rate of a crack) and the result of the actual measurement of the growth process of a crack occurring in a continuum (second correspondence information indicating the correspondence between the actual measurement value of the number of cycles and the actual measurement value of the growth rate of a crack), the Manson-Coffin law used in the simulation is changed. Thus, a simulation using a Manson-Coffin law changed based on the actual measurement result of the growth process of a crack occurring in a continuum can be performed, and a simulation result can be obtained with high accuracy for the growth process of a crack. As a result, the growth of a crack occurring in a continuum can be evaluated with high accuracy.

In addition, the crack growth evaluation apparatus repeats deleting a finite element or first changing the rigidity of the finite element and then analyzing stress and distortion when the cumulative value of the damage value of finite elements of a continuum is equal to or exceeds a threshold. When a finite element is deleted, the number of finite elements as analysis targets of a stress/distortion analysis can be decreased to speed up the speed of evaluating the growth of a crack occurring in a continuum. In addition, when the rigidity of a finite element is changed, the state of a growth of a crack occurring in a continuum can be evaluated without reproducing an analysis model.

The crack growth evaluation apparatus obtains the actual measurement value of the number of cycles of a load when the calculated growth rate of a crack and so on occurring in the continuum matches the actual measurement value and so on of the number of cycles of a load corresponding to the actual measurement value of the growth rate of a crack. Then, the apparatus calculates the nonlinear distortion amplitude value corresponding to the obtained actual measurement value of the number of cycles of a load based on a Manson-Coffin law, and obtains a new Manson-Coffin law based on the calculated nonlinear distortion amplitude value and the obtained actual measurement value of the number of cycles of a load. Thus, a growth rate of a crack occurring in the continuum can be easily calculated, and a long-life continuum can be designed with stability without unevenness by, for example, appropriately changing the shape of the continuum in designing the continuum.

In addition, the crack growth evaluation apparatus displays a state of a growth of a crack occurring in the continuum using an analysis model based on a result of the comparison between a cumulative value of a damage value of a finite element and a threshold. Thus, the state of a growth of a crack occurring in the continuum can be displayed with high accuracy.

BRIEF DESCRIPTION OF THE DRAWINGS

FIG. 6 is a diagram showing an example of coordinate point directive information.

FIG. 7 is a diagram showing an example of the information stored in a determination result information storage unit.

DETAILED DESCRIPTION OF THE PREFERRED EMBODIMENTS

Figure 1:
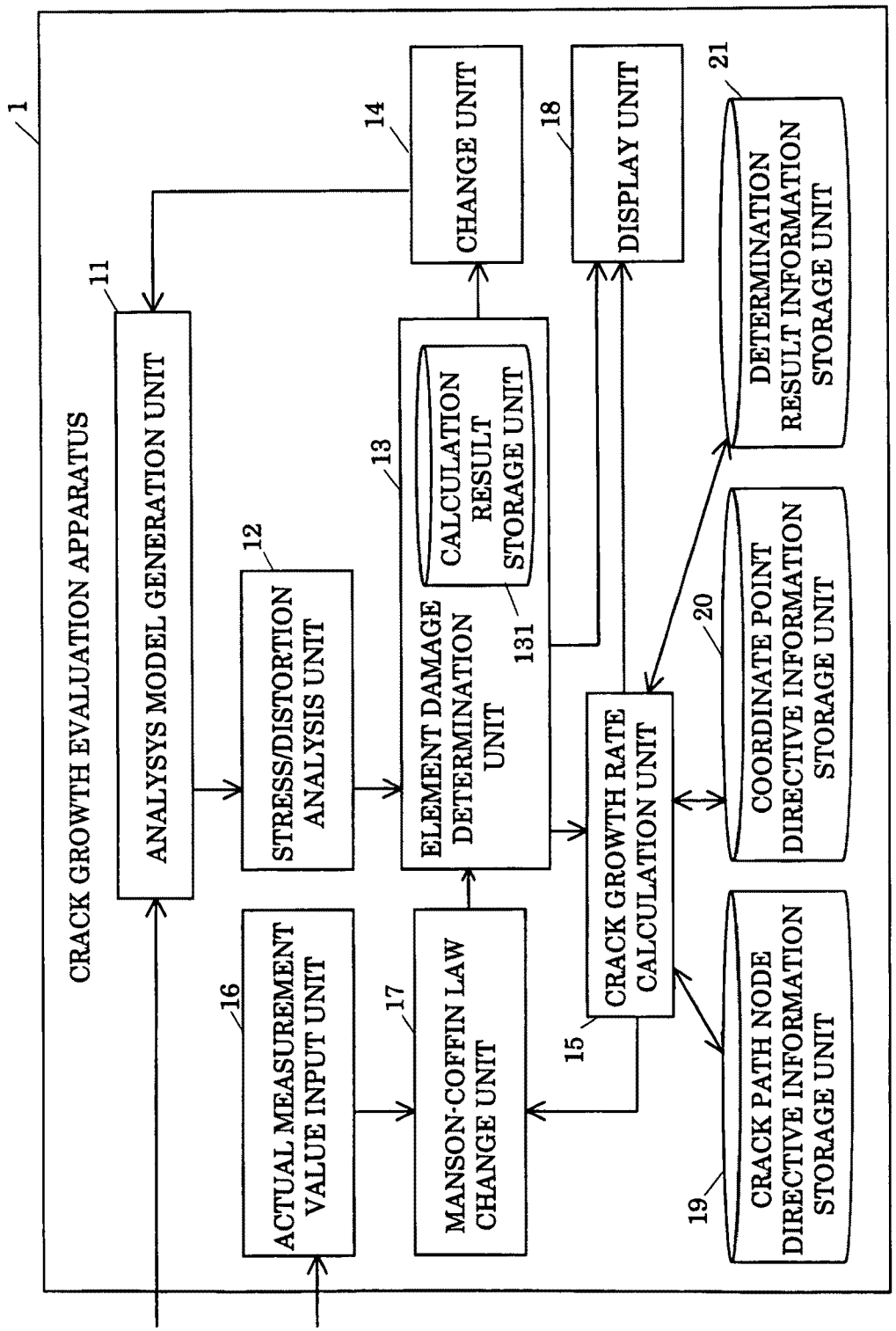
FIG. 1 is a diagram showing an example of a structure of the crack growth evaluation apparatus of the present embodiment.

FIG. 1 is a diagram showing an example of a structure of a crack growth evaluation apparatus of the present embodiment.

A crack growth evaluation apparatus 1 is a computer that evaluates a growth of a crack occurring in a continuum. The crack growth evaluation apparatus 1 includes an analysis model generation unit 11, a stress/distortion analysis unit 12, an element damage determination unit 13, a change unit 14, a crack growth rate calculation unit (hereinafter referred to as a calculation unit) 15, an actual measurement value input unit 16, a Manson-Coffin law change unit 17, a display unit 18, a crack path node directive information storage unit 19, a coordinate point directive information storage unit 20, and a determination result information storage unit 21. Each unit provided for the crack growth evaluation apparatus 1 is realized by a CPU and a program present in main memory and executed on the CPU.

The analysis model generation unit (hereinafter referred to as a generation unit) 11 generates an analysis model of a continuum whose crack growth is to be evaluated. The analysis model is a model (finite element model) used in an analysis of stress and distortion occurring in a continuum performed in a finite element method, and an analysis model obtained by dividing a continuum into a plurality of finite elements. That is, the analysis model is to be used in an analyzing process by the stress/distortion analysis unit 12.

Figure 17:
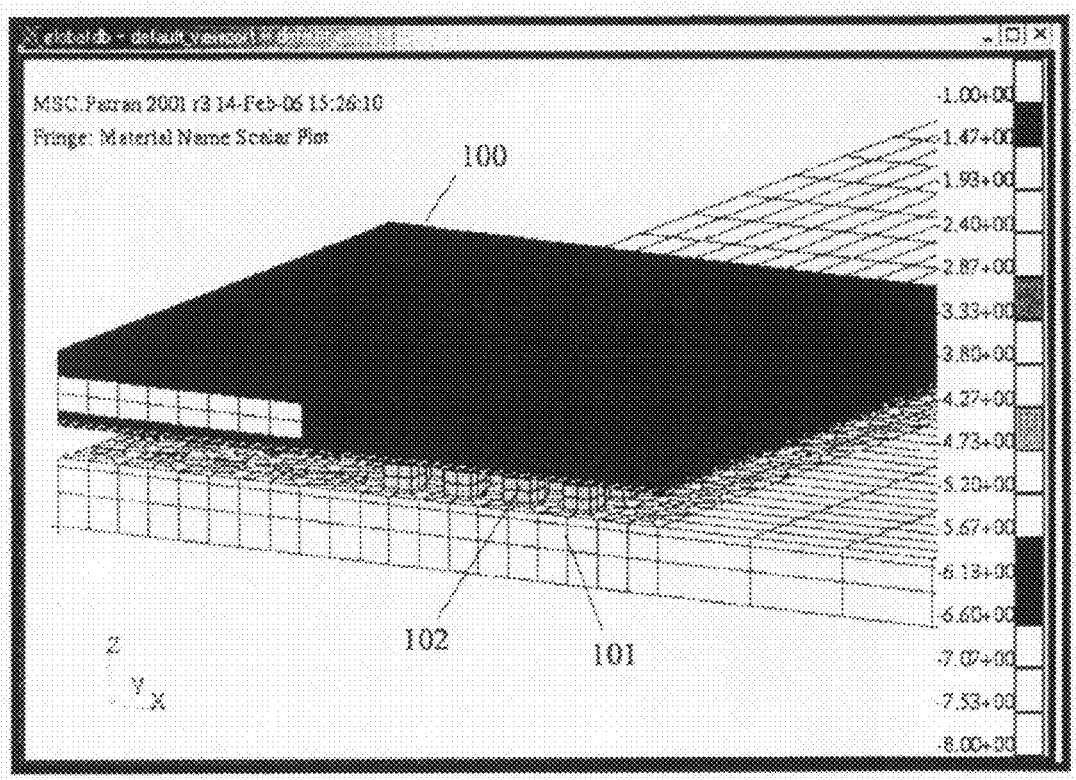
FIG. 17 is a diagram showing an analysis model of a BGA package.
Figure 18:
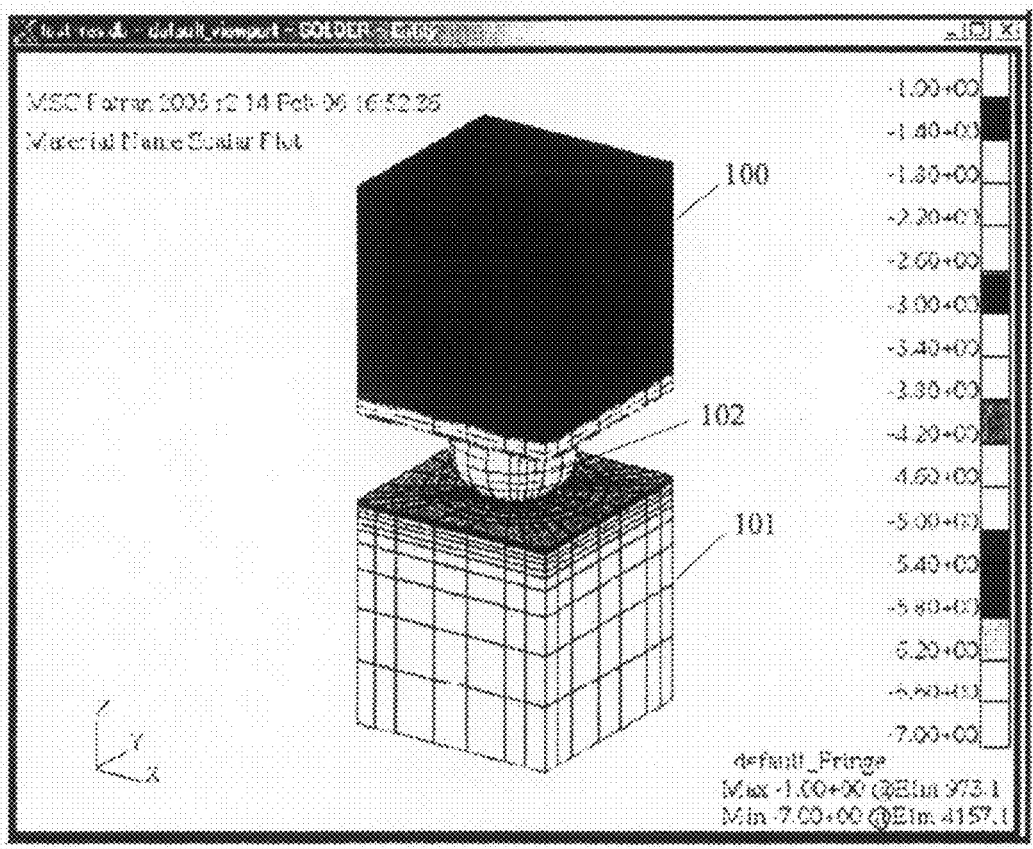
FIG. 18 is a diagram showing partially enlarged analysis model of a BGA package.
Figure 25:
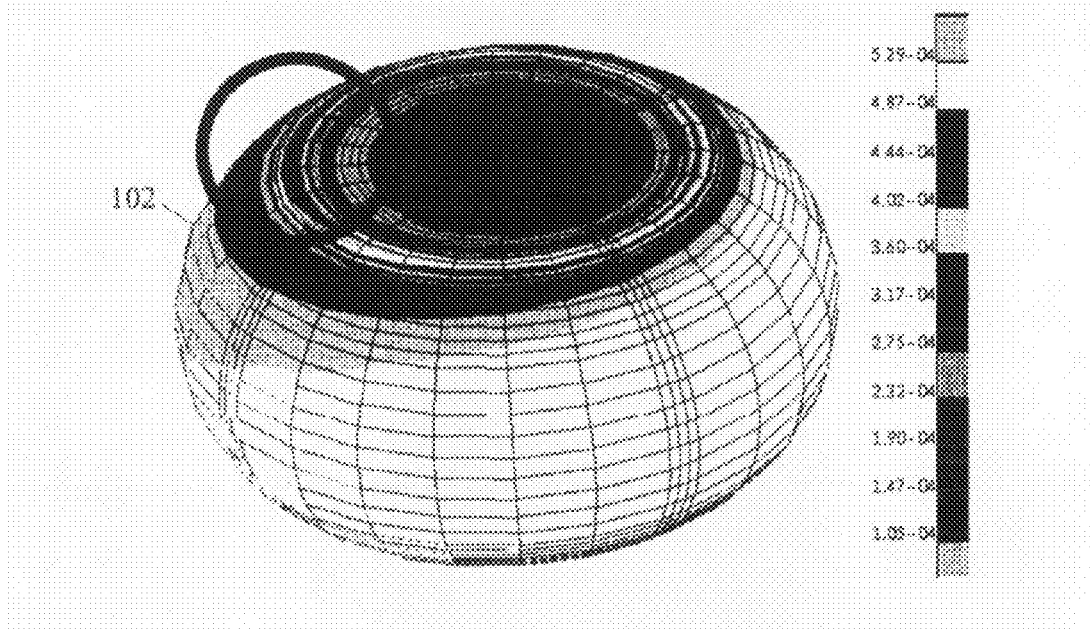
FIG. 25 is a diagram showing an analysis model of a soldered portion.

For example, the analysis model is generated for a soldered portion that joins an electronic part to a substrate. In this case, a soldered portion of an electronic part configures a continuum. The generation unit 11 generates an analysis model of a soldered portion according to electronic part information, substrate information, position information about a soldered portion, information about a load to be cyclically applied to the soldered portion, and information about a material of the soldered portion. The analysis model of the soldered portion is shown in FIGS. 17, 18, and 25. The generation unit 11 generates again an analysis model of a continuum when the change unit 14 described later deletes the finite elements of the continuum.

The stress/distortion analysis unit (hereinafter referred to as an analysis unit) 12 analyzes the stress and the distortion occurring in each of a plurality of finite elements of a continuum by a load cyclically applied to the continuum in a finite element method for each cycle of a load using an analysis model as it is well known. That is, the analysis unit 12 performs a stress/distortion analysis. The analysis result by the analysis unit 12 is transmitted to the element damage determination unit 13. A predetermined number of load cycles for a simulation are applied to the continuum. The stress/distortion analysis is performed on each of the predetermined number of cycles. The load is, for example, a temperature, a mechanical pressure and so on.

Practically, the analysis unit 12 obtains a cumulative equivalence creep distortion value and/or cumulative equivalence plasticity distortion value as the stress distortion for each of a plurality of finite elements of the continuum. The "cumulative correspondence" or "cumulative" creep distortion value are values obtained by accumulating the creep distortion value calculated in each cycle before the current cycle, and a cumulative value up to the current cycle. The same holds true with the plasticity distortion value.

Figure 2:
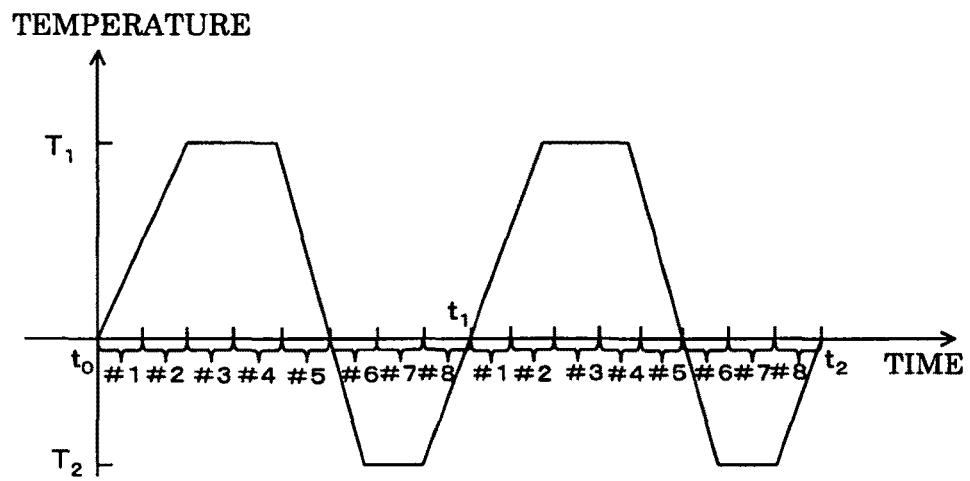
FIG. 2 is a diagram showing an example of a temperature cycle applied to a continuum.
Figure 19:
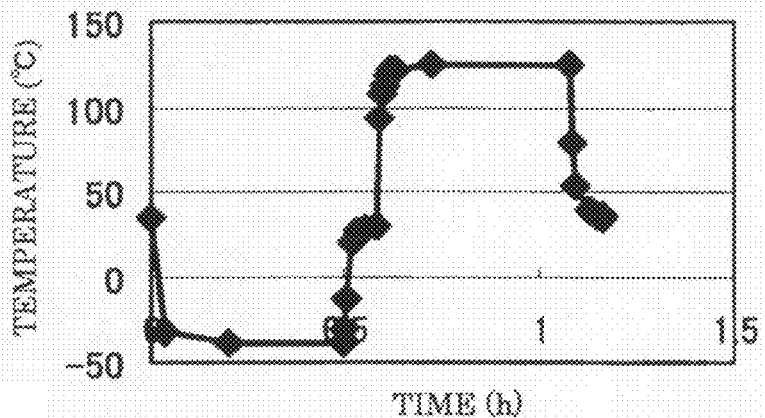
FIG. 19 is a diagram showing a temperature cycle applied to a soldered portion.
Figure 20:
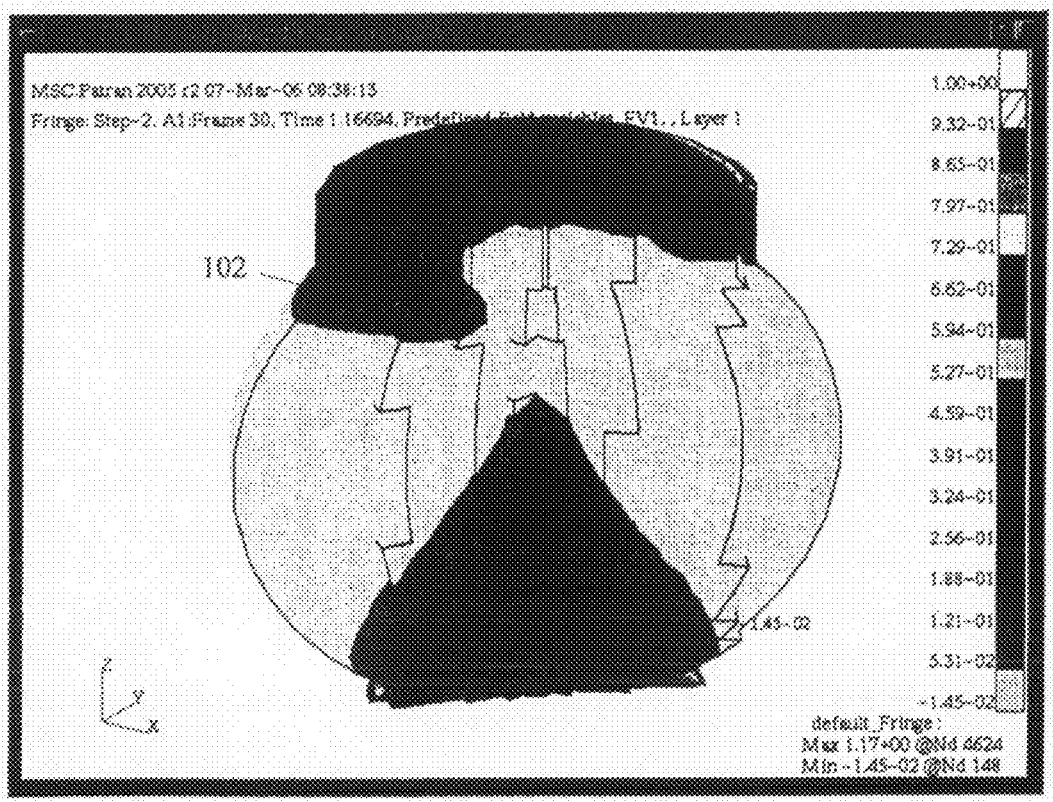
FIGS. 20, 21, 22, and 23 are diagrams showing a result of the simulation process according to the present embodiment.
Figure 21:
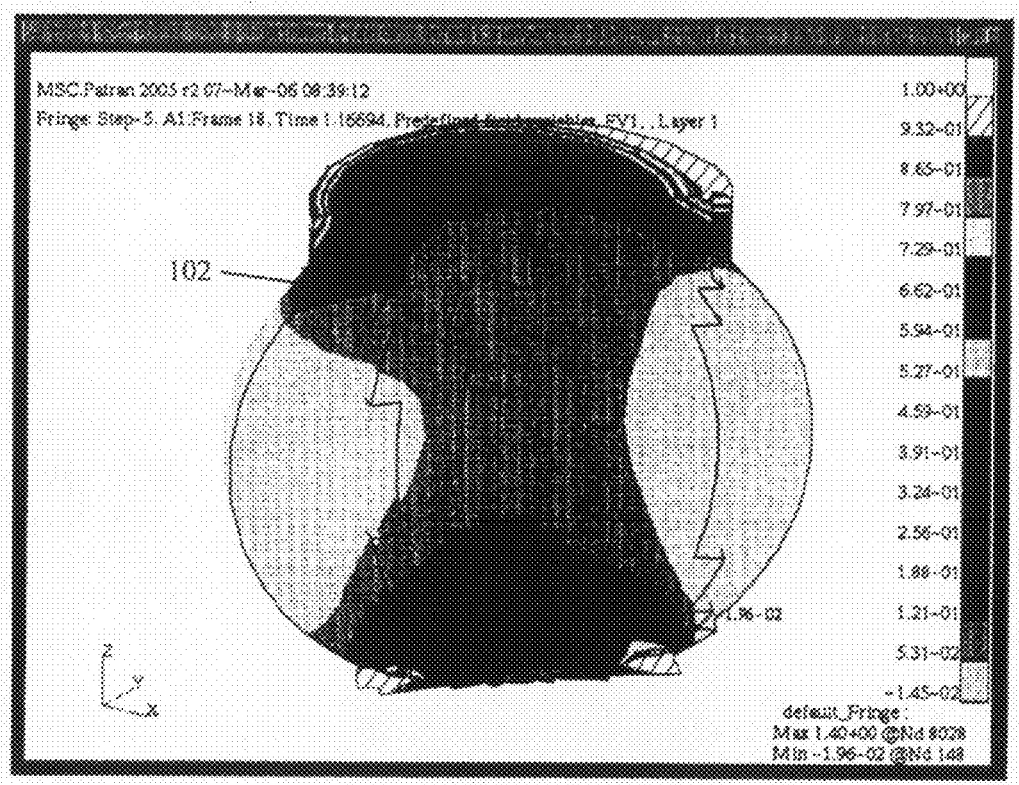
Figure 22:
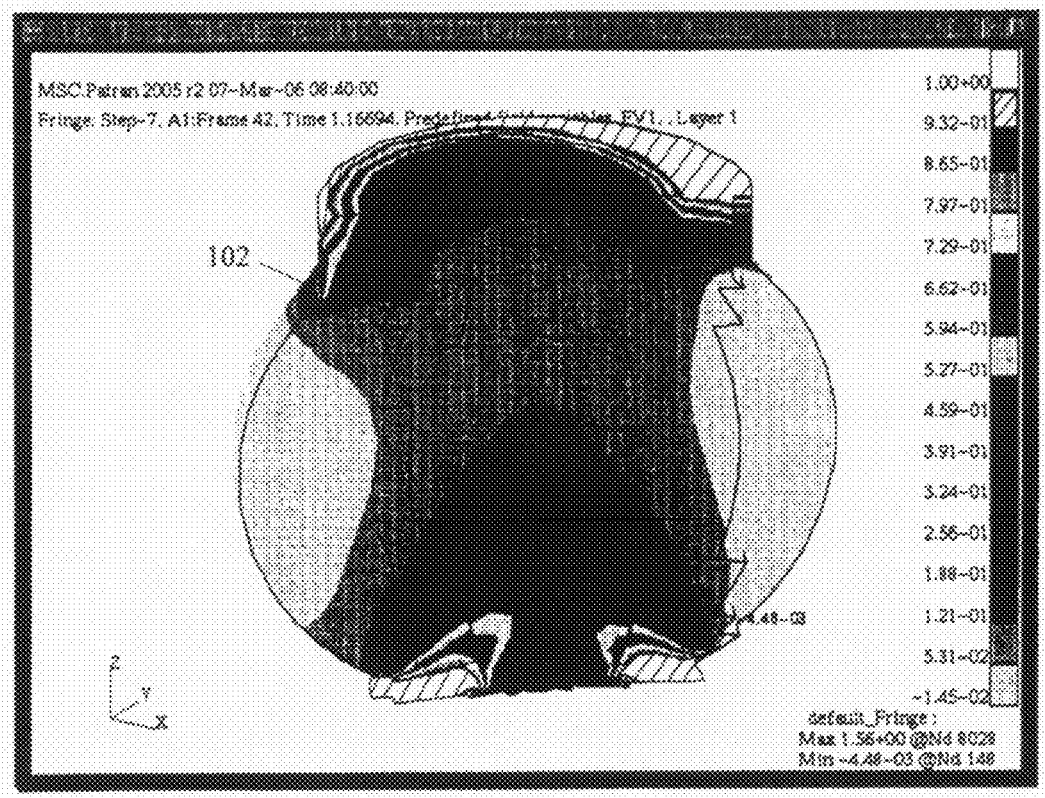
Figure 23:
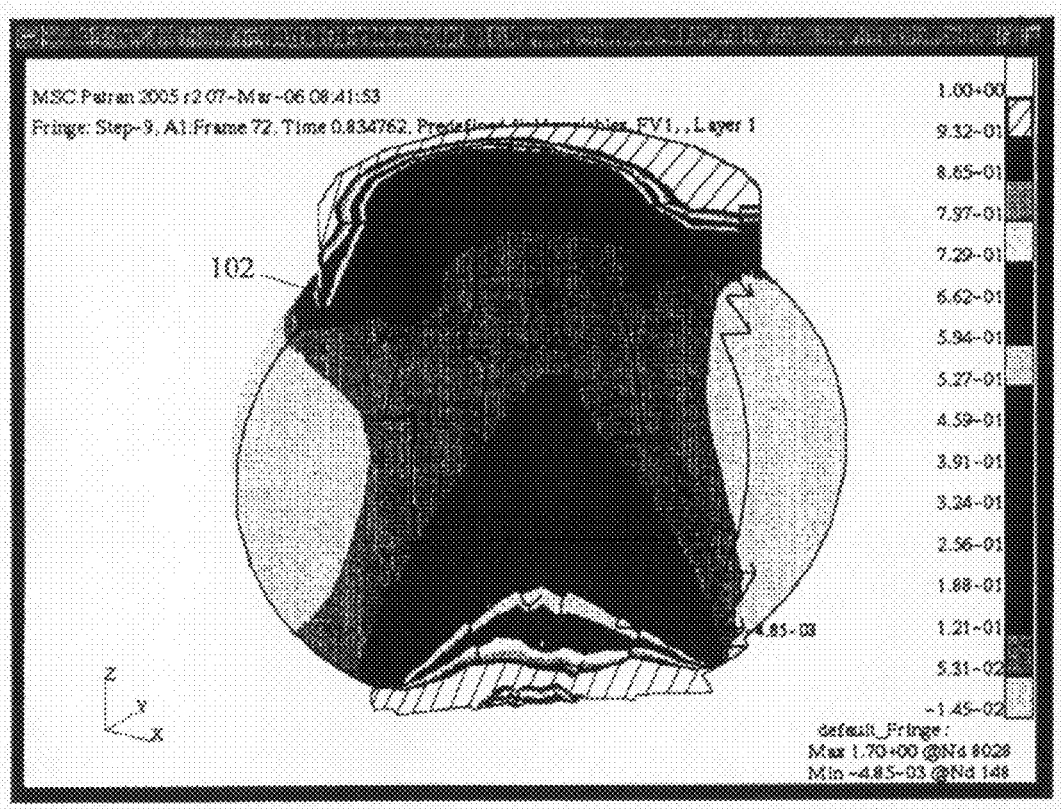

FIG. 2 is a diagram showing an example of a temperature cycle as an example of a load cycle applied to a continuum. FIG. 2 shows only the first temperature cycle (first cycle) and the second temperature cycle (second cycle) in the predetermined number of temperature cycles cyclically applied to a continuum. In this example, the first and second cycles are the cycles of the same load inclination, but they may be different from each other. Since the cycles in and after the third temperature cycle (third cycle) are similar to the first and/or second cycle, they are omitted in FIG. 2. FIG. 19 described later shows an example of an actual load cycle (temperature cycle).

In FIG. 2, time $t_0$ to time $t_1$ falls in the first temperature cycle (first cycle) and time $t_1$ to time $t_1$ falls in the second temperature cycle (second cycle). In the example shown in FIG. 2, a continuum is heated up to the temperature $T_1$ in each temperature cycle, held at the time $t_1$ for a predetermined time, cooled down to the temperature $T_2$, and is held at the temperature $T_2$ for a predetermined time. In FIG. 2, #1 to #8 refer to a time increment. The time increment is a time unit in the stress/distortion analyzing process by the generation unit 11 and the process of calculating a cumulative damage value D by the element damage determination unit 13.

In the load cycle cyclically applied to a continuum, the cycle to be currently treated in the stress/distortion analyzing process, the damage evaluating process and/or the rigidity changing process is referred to as a "current cycle". In addition, a cycle immediately before the current cycle is referred to as a "preceding cycle", and a cycle immediately after the current cycle is referred to as a "next cycle".

The element damage determination unit (hereinafter referred to as a determination unit) 13 calculates a cumulative nonlinear distortion value for each of a plurality of finite elements of a continuum in each load cycle cyclically applied to the continuum using the analysis model based on the analysis result from the analysis unit 12, and calculates a nonlinear distortion amplitude value based on the calculated cumulative nonlinear distortion value. Furthermore, the determination unit 13 calculates a damage value using a Manson-Coffin law based on the calculated nonlinear distortion amplitude value, calculates a cumulative value (cumulative damage value D) based on the calculated damage value, compares the cumulative damage value D with a predetermined threshold, and determines whether or not the cumulative damage value D is equal to or exceeds the threshold (or larger than the threshold). The determination unit 13 transmits a determination result (and cumulative damage value D) to the change unit 14, the calculation unit 15, and the display unit 18.

Practically, the determination unit 13 first calculates a cumulative nonlinear distortion value of the finite element based on the cumulative equivalence creep distortion value and/or cumulative equivalence plasticity distortion value of each of a plurality of finite elements of the continuum as it is well known, and stores the value in a calculation result storage unit 131 shown in FIG. 1.

Figure 3:
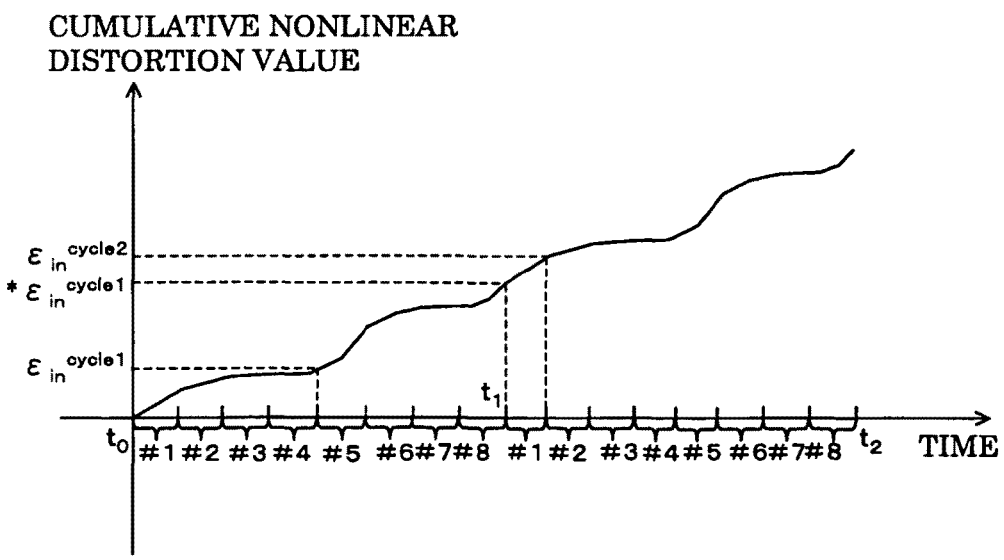
FIG. 3 is a diagram showing an example of a cumulative nonlinear distortion value.

FIG. 3 is a diagram showing an example of a cumulative nonlinear distortion value sequentially calculated by the determination unit with the lapse of time. This example shows a cumulative nonlinear distortion value when the temperature cycle shown in FIG. 2 is applied to a continuum. As shown in FIG. 3, the cumulative nonlinear distortion value increases with a lapse of time. In FIG. 3, $\epsilon_{in}^{cycle1}$ refers to a cumulative nonlinear distortion value during the calculation in the first cycle (when a damage value calculating process on the time increment #4 of the first cycle is terminated). $\epsilon_{in}^{cycle2}$ refers to a cumulative nonlinear distortion value during the calculation in the second cycle (when a damage value calculating process on the time increment #1 of the second cycle is terminated). $*\epsilon_{in}^{cycle1}$ refers to the final cumulative nonlinear distortion value (final cumulative nonlinear distortion value) in the first cycle.

Next, the determination unit 13 calculates the nonlinear distortion amplitude value on each of a plurality of finite elements of the continuum based on the cumulative nonlinear distortion value stored in the calculation result storage unit 131, and calculates a damage value of the finite element using a Manson-Coffin law based on the calculated value. The damage value is calculated in each load cycle. A cumulative damage value D refers to accumulated damage values up to the cycle (current cycle).

As nonlinear distortion amplitude value, for example, a value equal to a half of a cumulative nonlinear distortion value may be used. The value is not exactly a cumulative nonlinear distortion value, but does not largely affect a calculation result of the cumulative damage value D. By using the value equal to a half of a cumulative nonlinear distortion value, the processing time for calculation of a nonlinear distortion amplitude value can be shortened.

The half value of the cumulative nonlinear distortion value as a nonlinear distortion amplitude value can be replaced with the following calculated value. That is, the determination unit 13 subtracts the cumulative nonlinear distortion value in the preceding cycle to the current cycle from the cumulative nonlinear distortion value in the current cycle of the load cycle for each of a plurality of finite elements of a continuum. Then, the determination unit 13 sets the value calculated in the calculation (or the value obtained by dividing the calculated value by a predetermined value) as a nonlinear distortion amplitude value in the current cycle for each of a plurality of finite elements of the continuum.

Next, the determination unit 13 applies the Manson-Coffin law in the following equation to the nonlinear distortion amplitude value of the finite element and calculates the count of cyclic fatigue life of the finite element. The value is calculated for each load cycle.

$$Nf_i = C \cdot (\Delta\epsilon_i)^{-n} \ (1 \leq i \leq k) \quad \text{(equation 2)}$$

In the equation 2, $Nf_i$ refers to the count of cyclic fatigue life for the i-th load cycle (i-th cycle). $\Delta\epsilon_i$ refers to the nonlinear distortion amplitude value for the i-th cycle. C and n refer to parameters depending on the material and the shape of a continuum. When the term of the multiplier in the above-mentioned equation 1 is developed, an equation of multiplying the −n-th power of the nonlinear distortion amplitude value by a constant as shown by the equation 2 is obtained.

The determination unit 13 calculates $1/Nf_i = 1/C \cdot (\Delta\epsilon_1)^{-n}$ as a damage value for the i-th cycle. That is, a reciprocal of the count of cyclic fatigue life is obtained. Furthermore, the determination unit 13 calculates the cumulative damage value D by adding the damage value up to the cycle (current cycle) using the following equation 3, and stores the value in the calculation result storage unit 131.

$$D = 1/C \cdot (\Delta\epsilon_1)^{-n} + 1/C \cdot (\Delta\epsilon_2)^{-n} + \ldots + 1/C \cdot (\Delta\epsilon_k)^{-n} \quad \text{(equation 3)}$$

Furthermore, the determination unit 13 compares the cumulative damage value D stored in the calculation result storage unit 131 with a predetermined threshold (1 for example). A threshold can be empirically determined. The result of the comparison is transmitted to the calculation unit 15, the change unit 14, and the display unit 18.

In the present embodiment, the determination unit 13 optionally changes a parameter of a Manson-Coffin law (for example, parameters C and n of the Manson-Coffin law in the equation 2), obtains a plurality of Manson-Coffin laws, and performs a calculating process on the cumulative damage value D, a comparing process between a cumulative damage value D and the threshold, and a process of transmitting a comparison result to the calculation unit 15, the change unit 14, and the display unit 18 for each Manson-Coffin law obtained. When the determination unit 13 receives a new Manson-Coffin law after a change from the Manson-Coffin law change unit 17 described later, the determination unit 13 performs the process of calculating the cumulative damage value D, the process of comparing the cumulative damage value D with the threshold, and the process of transmitting the comparison result to the calculation unit 15, the change unit 14, and the display unit 18 based on the new Manson-Coffin law.

When the cumulative damage value D is equal to or exceeds the threshold, the change unit 14 deletes a finite element having the cumulative damage value D equal to or exceeding the threshold. The change unit 14 performs the process of deleting a finite element for each Manson-Coffin law obtained by the determination unit 13 optionally changing the parameter.

When the change unit 14 receives from the determination unit 13 a result of the process of comparing the cumulative damage value D calculated based on a new Manson-Coffin law obtained by the Manson-Coffin law change unit 17 with the threshold, the change unit 14 performs the process of deleting a finite element similar to the process performed for each Manson-Coffin law obtained by the determination unit 13. That is, when the change unit 14 performs the process of deleting a finite element on each Manson-Coffin law obtained by the determination unit 13 optionally changing a parameter, the change unit 14 also performs the process of deleting a finite element when the change unit 14 receives from the determination unit 13 a result of the process of comparing the cumulative damage value D based on a new Manson-Coffin law with the threshold.

After the change unit 14 deletes a finite element, the generation unit 11 reproduces an analysis model of the continuum, and the analysis unit 12 analyzes the stress and the distortion occurring in the next cycle after the current cycle of the load cycle in each of a plurality of finite elements of the continuum using the reproduced analysis model by a finite element method.

When the cumulative damage value D is less than the threshold, the change unit 14 does not delete a finite element corresponding to the cumulative damage value D.

When the change unit 14 deletes a finite element having a cumulative value of a damage value equal to or exceeding the threshold in the current cycle, the deleted finite element falls out of the target of the stress/distortion analyzing process of the analysis unit 12 in the next cycle. Therefore, there is smaller possibility that an error occurs in the stress/distortion analyzing process by the analysis unit 12 and the process of the determination unit 13 performed after the stress/distortion analyzing process. As a result, the process of the crack growth evaluation apparatus 1 of the present embodiment evaluating the growth of a crack occurring in the continuum can be performed without suspension in midstream.

The change unit 14 may change the rigidity (for example, a Young's modulus or yield stress) of a finite element having the cumulative damage value D equal to or exceeding the threshold to reduce the rigidity to a value close to 0 (for example, the 1/100 value of the initial value of the rigidity of the finite element). That is, the value of the rigidity of a finite element is not set to 0. Thus, in the stress/distortion analyzing process in the next cycle to the current cycle of the load cycle, for example, a cumulative equivalence creep distortion value and the cumulative equivalence plasticity distortion value can be prevented from becoming an exceedingly large value (unreasonable value).

When the change unit 14 performs the process of changing the rigidity of a finite element on each Manson-Coffin law obtained by the determination unit 13 optionally changing a parameter, the change unit 14 performs the process of changing the rigidity of a finite element when the change unit 14 receives from the determination unit 13 a result of the process of comparing the cumulative damage value D based on a new Manson-Coffin law with a threshold.

The calculation unit 15 calculates a growth rate of a crack occurring in the continuum on each load cycle based on a determination result of the determination unit 13 when the load cycle terminates. Based on the growth rate of a crack, the calculation unit 15 obtains the information (first correspondence information) about the correspondence between the number of cycles of a load cyclically applied to the continuum and the growth rate of a crack.

Practically, the calculation unit 15 obtains the first correspondence information as described below. First, the calculation unit 15 stores in the determination result information storage unit 21 the determination result (and the cumulative damage value D) by the determination unit 13 as to whether or not the cumulative damage value D is equal to or exceeds the threshold. Furthermore, the calculation unit 15 designates a growth path of a crack occurring in the continuum based on the crack path node directive information stored in advance in the crack path node directive information storage unit 19 described later. Practically, the calculation unit 15 designates (the information about) the node arranged on the growth path of a crack occurring in a continuum. The crack path node directive information is information indicating the growth path of a crack occurring in a continuum. The crack path node directive information includes the identification information of a node of a finite element (for example, a node number) arranged on the growth path of a crack.

In addition, the calculation unit 15 obtains the coordinates of the node on the designated growth path of a crack based on the coordinate point directive information stored in advance in the coordinate point directive information storage unit 20 described later. The coordinate point directive information is coordinate information corresponding to each node.

The calculation unit 15 determines whether or not the extrapolated value of the cumulative damage value D of the node (for example, a node having the smallest node number) arranged in the starting position of the growth path of a crack among nodes on the designated growth path of a crack is equal to or exceeds the threshold based on the determination result stored in the determination result information storage unit 21. When the calculation unit 15 determines that the extrapolated value of the cumulative damage value D of the node arranged at the starting position of the growth path of a crack is equal to or exceeds the threshold, the calculation unit 15 sets the node arranged in the starting position of the growth path of a crack as a node at which the crack starts. When the cumulative damage value D of the node arranged at the starting position of the growth path of a crack is less than the threshold, the calculation unit 15 determines that the length of the crack of the growth path of the crack is 0 (no crack occurs).

Then, the calculation unit 15 sequentially determines whether or not the cumulative damage value D of a node is equal to or exceeds the threshold from the next node after the node where the crack starts on the growth path of a crack, and calculates the length of the path from the node where the crack starts to the last node whose cumulative damage value D is equal to or exceeds the threshold as a length of the crack occurring in a continuum. That is, the calculation unit 15 determines whether or not the cumulative damage value D of each node is equal to or exceeds the threshold in the order of the arrangement on the growth path of a crack, and determines up to which node the cumulative damage value D is equal to or exceeds the threshold. For example, when the i-th node on the growth path of a crack is the last node whose cumulative damage value D is equal to or exceeds the threshold, the calculation unit 15 calculates the length of the path from the node where a crack starts to the i-th node based on the coordinate information about the designated node, and outputs the calculated path length as the length of the crack.

Furthermore, the calculation unit 15 calculates the total length of the growth path of the crack according to the coordinate information about the determined node. Then, the calculation unit 15 calculates the rate of the calculated length of the crack to the calculated total length of the growth path of a crack as the growth rate of the crack occurring in the continuum. The first correspondence information is obtained in the process of calculating the growth rate of the crack by the calculation unit 15.

In the present embodiment, the calculation unit 15 obtains the first correspondence information for each Manson-Coffin law based on a result of the process of comparing the cumulative damage value D for each Manson-Coffin law obtained by the determination unit 13 optionally changing the parameter with the threshold. When the calculation unit 15 receives from the determination unit 13 the result of the process of comparing the cumulative damage value D calculated based on a new Manson-Coffin law obtained by the Manson-Coffin law change unit 17 with the threshold, the calculation unit 15 obtains the first correspondence information based on the result of the comparing process.

The actual measurement value input unit 16 inputs the information (second correspondence information) about the correspondence between the actual measurement value of the number of cycles of a load cyclically applied to the continuum and the actual measurement value of the growth rate of a crack occurring in the continuum when the load is applied for the number of cycles to the continuum.

The Manson-Coffin law change unit 17 changes the Manson-Coffin law based on the first correspondence information obtained by the calculation unit 15 and the second correspondence information input by the actual measurement value input unit 16.

Practically, the Manson-Coffin law change unit 17 obtains the actual measurement value of the number of cycles of a load when the growth rate of a crack calculated by the calculation unit 15 and the number of cycles of a load corresponding to the growth rate of a crack respectively match the actual measurement value of the growth rate of a crack and the actual measurement value of the number of cycles of a load corresponding to the actual measurement value of the growth rate of a crack, and calculates (inverse operation) the nonlinear distortion amplitude value corresponding to the actual measurement value of the number of cycles of a load based on the Manson-Coffin law used by the determination unit 13 calculating the damage value.

In the present embodiment, the Manson-Coffin law change unit 17 calculates the nonlinear distortion amplitude value corresponding to the actual measurement value of the number of cycles of a load for each Manson-Coffin law obtained by the determination unit 13 optionally changing a parameter. Then, the Manson-Coffin law change unit 17 determines a new parameter by performing, for example, the least square approximation based on the nonlinear distortion amplitude value calculated for each Manson-Coffin law and the actual measurement value of the number of cycles of a load. The Manson-Coffin law change unit 17 changes a Manson-Coffin law by obtaining a new Manson-Coffin law based on the determined new parameter. In addition, after the change, the Manson-Coffin law change unit 17 transmits the new Manson-Coffin law to the determination unit 13.

The display unit 18 displays a state of a growth of a crack occurring in the continuum using an analysis model based on a determination result as to whether or not the cumulative damage value D by the determination unit 13 is equal to or exceeds the threshold. The state of a growth of a crack is displayed by displaying the cumulative damage value D for each of a plurality of finite elements of a continuum. The state of a growth of a crack is shown in FIGS. 20 to 23 described later.

The display unit 18 may display the state of a growth of a crack occurring in the continuum for each of predetermined one or more load cycles. That is, the display of the state of a growth of a crack on the display unit 18 is updated for each cycle or plural cycles (for example, ten cycles), and the number of cycles of updated display is predetermined (the same holds true with the following descriptions).

Figure 24:
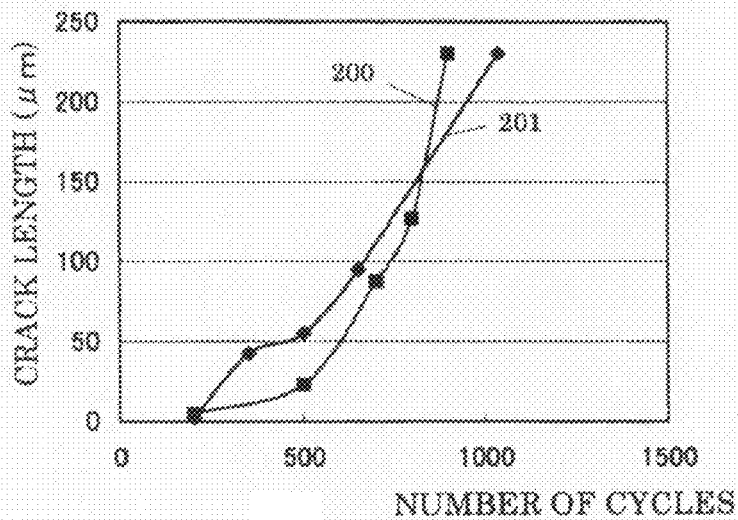
FIG. 24 is a diagram showing an example of the display of the length of a crack occurring in a soldered portion for each number of cycles.

The display unit 18 may display the first correspondence information calculated by the calculation unit 15. In addition, the display unit 18 may display the length of a crack occurring in the continuum calculated by the calculation unit 15. The length of the crack occurring in the continuum is shown in FIG. 24 described later, for example.

The crack path node directive information storage unit 19 stores crack path node directive information in advance. The coordinate point directive information storage unit 20 stores coordinate point directive information in advance. The determination result information storage unit 21 stores a determination result by the determination unit 13.

A program that realizes the crack growth evaluation apparatus 1 according to the present embodiment can be stored in a computer-readable record medium, for example, semiconductor memory, a hard disk, CD-ROM, a DVD, and so on, and is provided after recorded in any of these record media, or can be provided by the transmission and reception over a network through a communication interface.

Figures 4, 5:
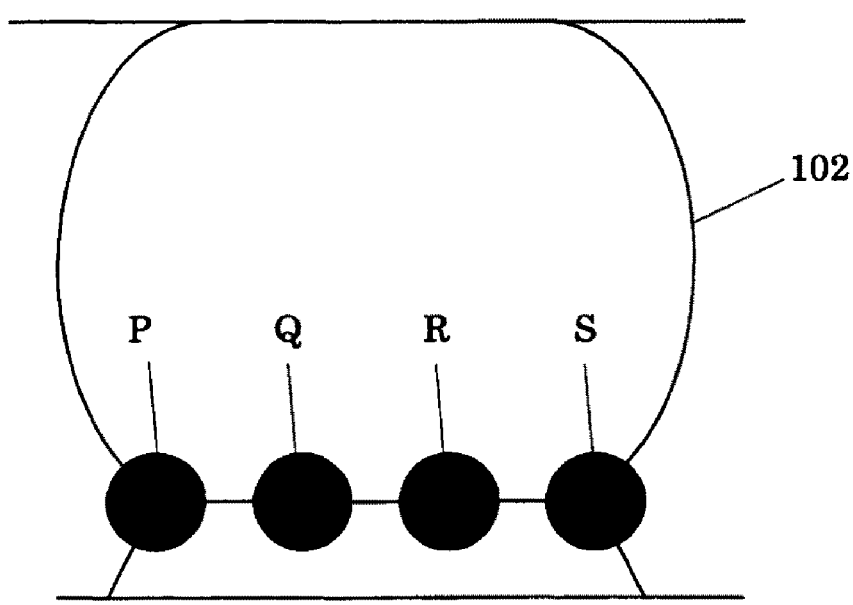
FIG. 4 is a diagram showing an example of crack path node directive information.
FIG. 5 is a diagram showing an example of a soldered portion.

FIG. 4 is a diagram showing an example of crack path node directive information stored in advance in the crack path node directive information storage unit. The crack path node directive information shown in FIG. 4 includes the information about a growth path of a crack for each continuum. Each number connected by an arrow mark predetermined in an item of the growth path of a crack shown in FIG. 4 indicates the node number of a node of a finite element arranged on the growth path of a crack. The node number is identification information about the node of a finite element. The path indicated by the arrow mark connecting each node number set in the item of the growth path of a crack indicates a growth path of a crack. For example, "1→2→3→4" set in the item of the growth path of a crack about the continuum A indicates that the growth path of a crack for the continuum A starts from the node having the node number 1, and terminates at the node having the node number 4 through the node having the node number 2 and the node having the node number 3.

For example, when the continuum A is the soldered portion 102 shown in FIG. 5, the node P having the node number 1 of the soldered portion 102 is the node arranged at the starting position of the growth path of a crack of the soldered portion 102. Then, the path starting at the node P and ending at the node S having the node number 4 through the node Q having the node number 2 and the node R having the node number 3 is the growth path of a crack.

FIG. 6 is a diagram showing an example of coordinate point directive information stored in advance in the coordinate point directive information storage unit. The coordinate point directive information includes coordinate information for each node number. For example, the coordinates of the node number 1 shown in FIG. 5 are (a, b, c).

FIG. 7 is a diagram showing an example of information stored in the determination result information storage unit. As shown in FIG. 7, the determination result information storage unit 21 stores the cumulative damage value D calculated by the determination unit 13 and a determination result by the determination unit 13 as associated with a finite element and a node number. In FIG. 7, the item of the finite element sets identification information about a finite element. The item of a node number sets a node number. The item of a cumulative damage value D sets the cumulative damage value D of (the node of) the finite element. The item of a determination result sets the information indicating whether or not the cumulative damage value D of (the node of) the finite element is equal to or exceeds a threshold (1 for example). For example, the value "1" set in the item of a determination result indicates that the cumulative damage value D of (the node of) the finite element is equal to or exceeds 1. The value "0" set in the item of a determination result indicates that the cumulative damage value D of (the node of) the finite element is less than 1.

Figure 8:
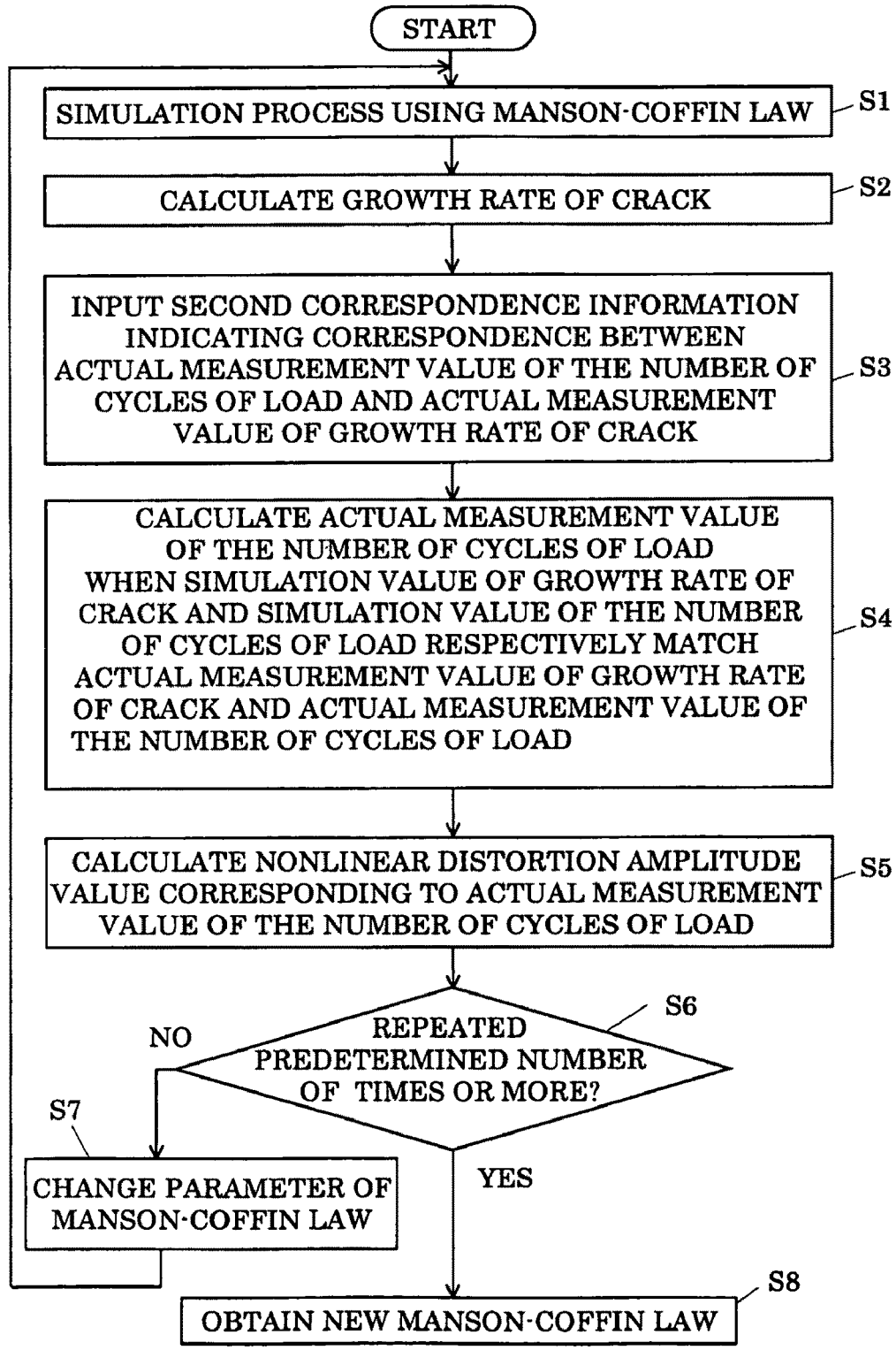
FIG. 8 is a diagram showing an example of a flow of a crack growth evaluating process.

FIG. 8 is a diagram showing an example of a flow of the crack growth evaluating process by the crack growth evaluation apparatus according to the present embodiment. First, the crack growth evaluation apparatus 1 optionally sets a parameter of a Manson-Coffin law, and performs a simulation process using the Manson-Coffin law (step S1). Practically, the simulation process in the step Si includes the stress/distortion analyzing process by the analysis unit 12, the process of calculating a cumulative damage value D using a Manson-Coffin law and the process of comparing the cumulative damage value D with the threshold by the determination unit 13, the process of deleting a finite element by the change unit 14, and the process of displaying the growth process of a crack by the display unit 18. The simulation process in the step S1 is performed on each load cycle.

The calculation unit 15 of the crack growth evaluation apparatus 1 calculates the growth rate of a crack based on the simulation process in the step S1 (step S2), and obtains the first correspondence information indicating the correspondence between the number of cycles of a load and the growth rate of a crack. Hereinafter, the growth rate of a crack calculated in the step S2, and the number of cycles of a load corresponding to the growth rate of a crack are respectively referred to as a simulation value of the growth rate of a crack and a simulation value of the number of cycles of a load.

Next, the actual measurement value input unit 16 inputs the second correspondence information indicating the correspondence between the actual measurement value of the number of cycles of a load and the actual measurement value of the growth rate of a crack (step S3). The Manson-Coffin law change unit 17 calculates the actual measurement value of the number of cycles of a load when the simulation value of the growth rate of a crack obtained in the step S2 and the simulation value of the number of cycles of a load respectively match the actual measurement value of the growth rate of a crack input in the step S3 and the actual measurement value of the number of cycles of a load corresponding to the actual measurement value of the growth rate of a crack (step S4). The process in the step S4 is described below with reference to FIG. 9A.

Figure 9A:
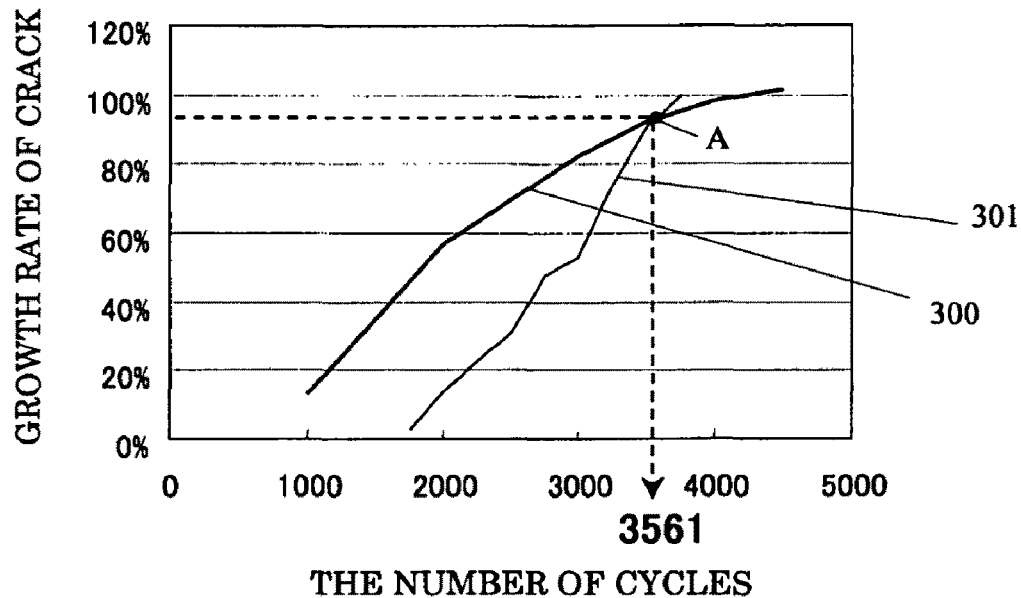
FIGS. 9A and 9B are diagrams showing a correspondence between the number of cycles of a load and the growth rate of a crack.

FIG. 9A shows a correspondence between the number of cycles of a load and the growth rate of a crack. The vertical axis shown in FIG. 9A indicates the growth rate of a crack, and the horizontal axis indicates the number of cycles of a load (the same holds true in FIG. 9B, and FIG. 12).

In FIG. 9A, a graph 300 shows the second correspondence information indicating the correspondence between the actual measurement value of the number of cycles of a load and the actual measurement value of the growth rate of a crack input in the step S3. Hereinafter, the graph 300 is referred to as an actual measurement value graph. A graph 301 shows the second correspondence information indicating the correspondence between the number of cycles of a load and the growth rate of a crack obtained in the step S2. Hereinafter, the graph 301 is referred to as a simulation graph. That is, the simulation graph 301 shows the first correspondence information obtained based on a result of a simulation process performed by the calculation unit 15 using a Manson-Coffin law having an optionally set parameter. The simulation graph 301 is a simulation graph obtained in the first process in the step S2.

The calculation unit 15 calculates a value of the number of cycles ("3561" in the example shown in FIG. 9A) corresponding to the point A as an intersection of the actual measurement value graph 300 and the simulation graph 301 shown in FIG. 9A.

Back in FIG. 8, the Manson-Coffin law change unit 17 substitutes the actual measurement value of the number of cycles of a load obtained in the step S4 for the Manson-Coffin law used in the simulation process in the step S1, and calculates the nonlinear distortion amplitude value corresponding to the actual measurement value of the number of cycles of a load (step S5). That is, the Manson-Coffin law change unit 17 performs the process in the step S5, and obtains the second correspondence information indicating the correspondence between the actual measurement value of the number of cycles of a load and the nonlinear distortion amplitude value. Practically, the Manson-Coffin law change unit 17 substitutes the number of cycles Nf=3561 corresponding to the point A in FIG. 9A for the Manson-Coffin law (for example, Nf=450*

($\Delta\epsilon/0.017545)^{-0.99}$) used in the simulation process in the step S1, and calculates, for example, $\Delta\epsilon=0.0022$ as the nonlinear distortion amplitude value $\Delta\epsilon$ corresponding to the number of cycles Nf=3561.

The Manson-Coffin law change unit 17 determines whether or not the process in the steps S1 to S5 has been repeated a predetermined number of times (four times for example) in step S6. Practically, the Manson-Coffin law change unit 17 determines whether or not a predetermined number or more of the nonlinear distortion amplitude value corresponding to the actual measurement value of the number of cycles of a load have been obtained. When the predetermined number of times or more of the nonlinear distortion amplitude value corresponding to the actual measurement value of the number of cycles of a load have been obtained, the Manson-Coffin law change unit 17 determines that the process in the steps S1 to S5 has been repeated a predetermined number or more. When the predetermined number of times or more of the nonlinear distortion amplitude value corresponding to the actual measurement value of the number of cycles of a load have not been obtained, the Manson-Coffin law change unit 17 determines that the process in the steps S1 to S5 has not been repeated a predetermined number or more.

When the Manson-Coffin law change unit 17 determines that the process in the steps S1 to S5 has not been repeated a predetermined number of times or more, the determination unit 13 changes the parameter of the Manson-Coffin law used in the simulation process in the step S1 (step S7), and the process in and after the step S1 is repeated.

When the Manson-Coffin law change unit 17 determines that the process in the steps S1 to S5 has been repeated a predetermined number of times or more, the Manson-Coffin law change unit 17 obtains a new Manson-Coffin law using the least square approximation based on the correspondence information between the actual measurement value of the number of cycles of a load for the predetermined number of times and the nonlinear distortion amplitude value obtained by repeating the process in the step S5 the predetermined number of times (step S8).

Figure 9B:
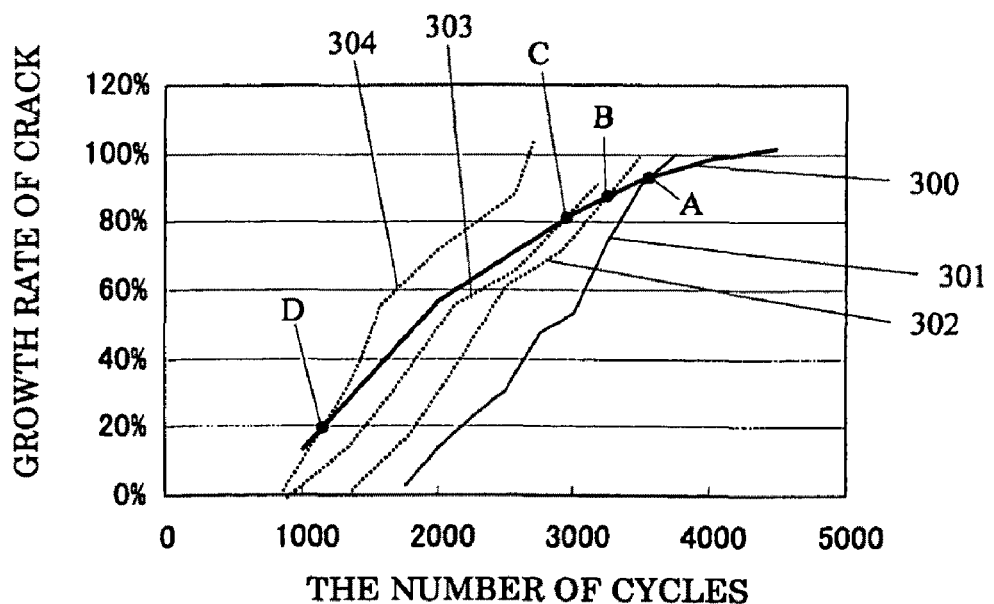

The process in the step S8 is described below with reference to FIGS. 9B and 10. FIG. 9B shows the first correspondence information as FIG. 9A. The simulation graphs (hereinafter referred to as graphs) 301, 302, 303, and 304 are obtained by repeating the process in the step S2 a predetermined number of times. For example, the graphs 301, 302, 303, and 304 are obtained in the first, second, third, and fourth process in the step S2.

By repeating the process in the step S4 a predetermined number of times, the calculation unit 15 calculates, in addition to the above-mentioned value of the number of cycles corresponding to point A, the value of the number of cycles corresponding to the point B as an intersection of the actual measurement value graph 300 and the graph 302, the value of the number of cycles corresponding to the point C as an intersection of the actual measurement value graph 300 and the graph 303, and the value of the number of cycles corresponding to the point D as an intersection of the actual measurement value graph 300 and the graph 304.

Then, by repeating the process in the step S5 a predetermined number of times, the Manson-Coffin law change unit 17 calculates the nonlinear distortion amplitude value corresponding to the number of cycles corresponding to the point A as described above, the nonlinear distortion amplitude value corresponding to the number of cycles corresponding to the point B, the nonlinear distortion amplitude value corresponding to the number of cycles corresponding to the point C, and the nonlinear distortion amplitude value corresponding to the number of cycles corresponding to the point D.

Figure 10:
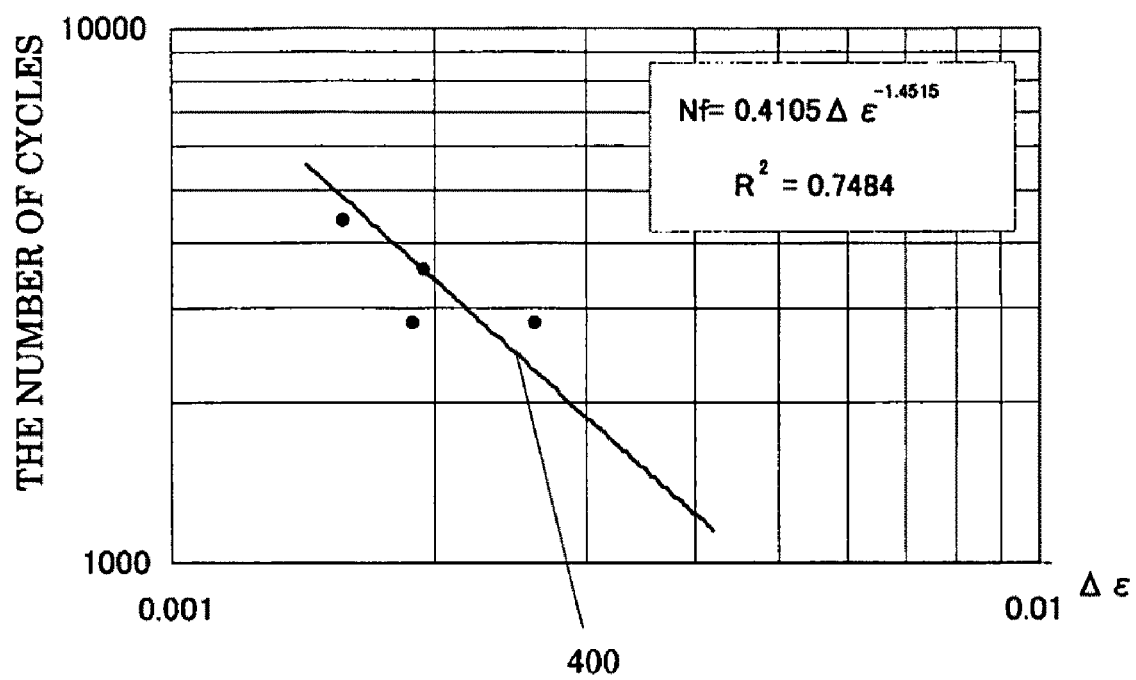
FIG. 10 is a diagram showing a correspondence between the number of cycles and the nonlinear distortion amplitude value.

FIG. 10 is a diagram showing a correspondence between the number of cycles and the nonlinear distortion amplitude value. The vertical axis in FIG. 10 indicates the number of cycles (Nf), and the horizontal axis indicates the nonlinear distortion amplitude $\Delta\epsilon$. The four points shown in FIG. 10 are obtained by respectively plotting the nonlinear distortion amplitude value corresponding to the number of cycles corresponding to the point A, the nonlinear distortion amplitude value corresponding to the number of cycles corresponding to the point B, the nonlinear distortion amplitude value corresponding to the number of cycles corresponding to the point C, and the nonlinear distortion amplitude value corresponding to the number of cycles corresponding to the point D shown in FIG. 9B. The Manson-Coffin law change unit 17 obtains a graph 400 indicating a new Manson-Coffin law shown in FIG. 10 using the least square approximation based on the coordinates of the four points plotted in FIG. 10. For example, the Manson-Coffin law change unit 17 obtains $N_f = 0.4105 \Delta\epsilon^{-1.4515}$ as a new Manson-Coffin law.

Figure 11:
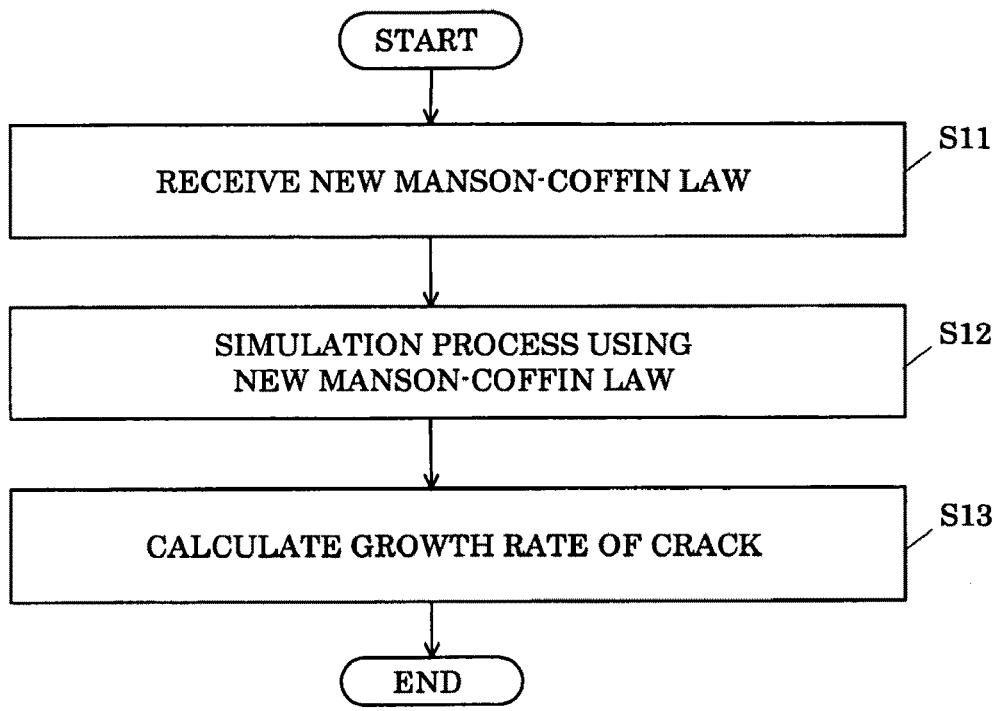
FIG. 11 is a diagram showing a flow of the crack growth evaluating process using a new Manson-Coffin law.

FIG. 11 is a diagram showing a flow of the crack growth evaluating process using a new Manson-Coffin law obtained by the Manson-Coffin law change unit.

The determination unit 13 receives a new Manson-Coffin law (for example, $N_f = 0.4105 \Delta\delta^{-1.4515}$) from the Manson-Coffin law change unit 17 (step S11). Then, the crack growth evaluation apparatus 1 performs a simulation process similar to the simulation process in the step S1 shown in FIG. 8 using the new Manson-Coffin law received in the step S11 (step S12). Practically, the analysis unit 12 performs the stress/distortion analyzing process, and the determination unit 13 performs the process of calculating the cumulative damage value D using a new Manson-Coffin law, the process of comparing the cumulative damage value D with the threshold, the change unit 14 performs the process of deleting a finite element, and the display unit 18 performs the process of displaying a state of a growth of a crack.

The calculation unit 15 calculates the growth rate of a crack based on a result of the simulation process in the step S12 (step S13), and obtains the first correspondence information (obtains a graph).

Figure 12:
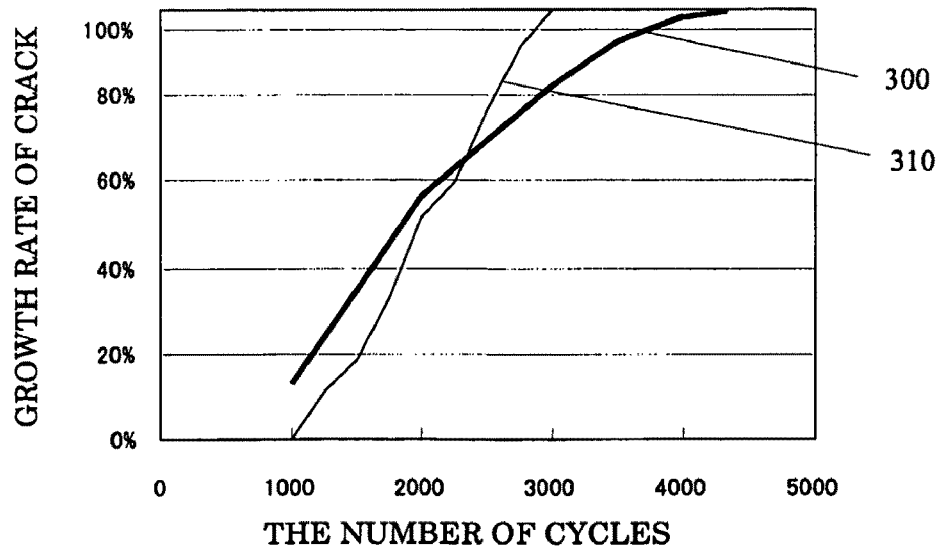
FIG. 12 is a diagram showing first correspondence information indicating the correspondence between the number of cycles of a load and the growth rate of a crack.

FIG. 12 is a diagram showing the first correspondence information obtained by the process in the step S13 shown in FIG. 11. FIG. 12 shows the graph 310 obtained in the process in the step S13 shown in FIG. 11. For comparison with the graph 310, the above-mentioned actual measurement value graph 300 is shown. With reference to 12, it is proved that the graph 310 closer to the actual measurement value graph 300 is obtained by performing the simulation process using a new Manson-Coffin law.

Figure 13:
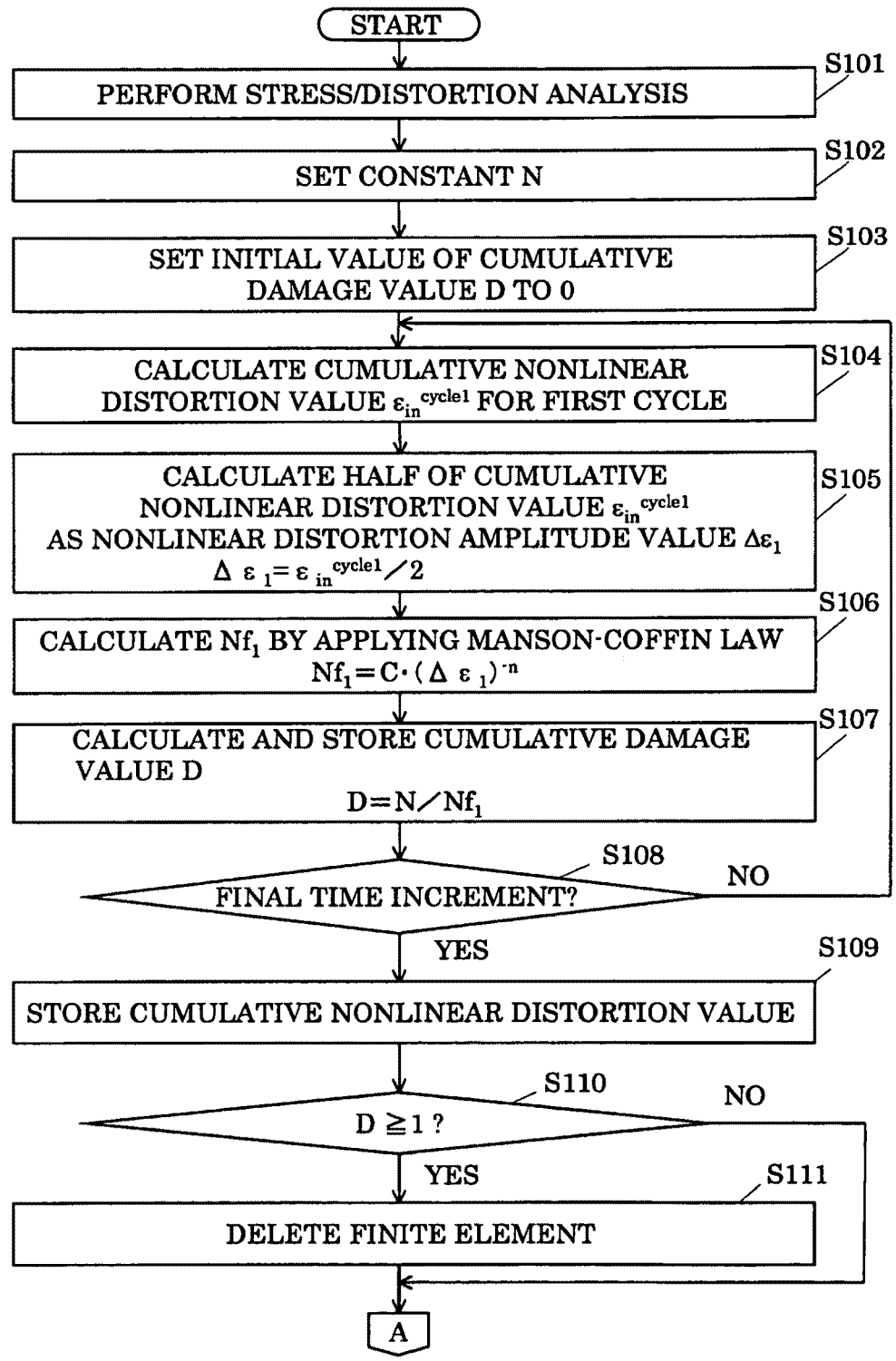
FIGS. 13 and 14 show an example of a flowchart showing the details of the simulation process.
Figure 14:
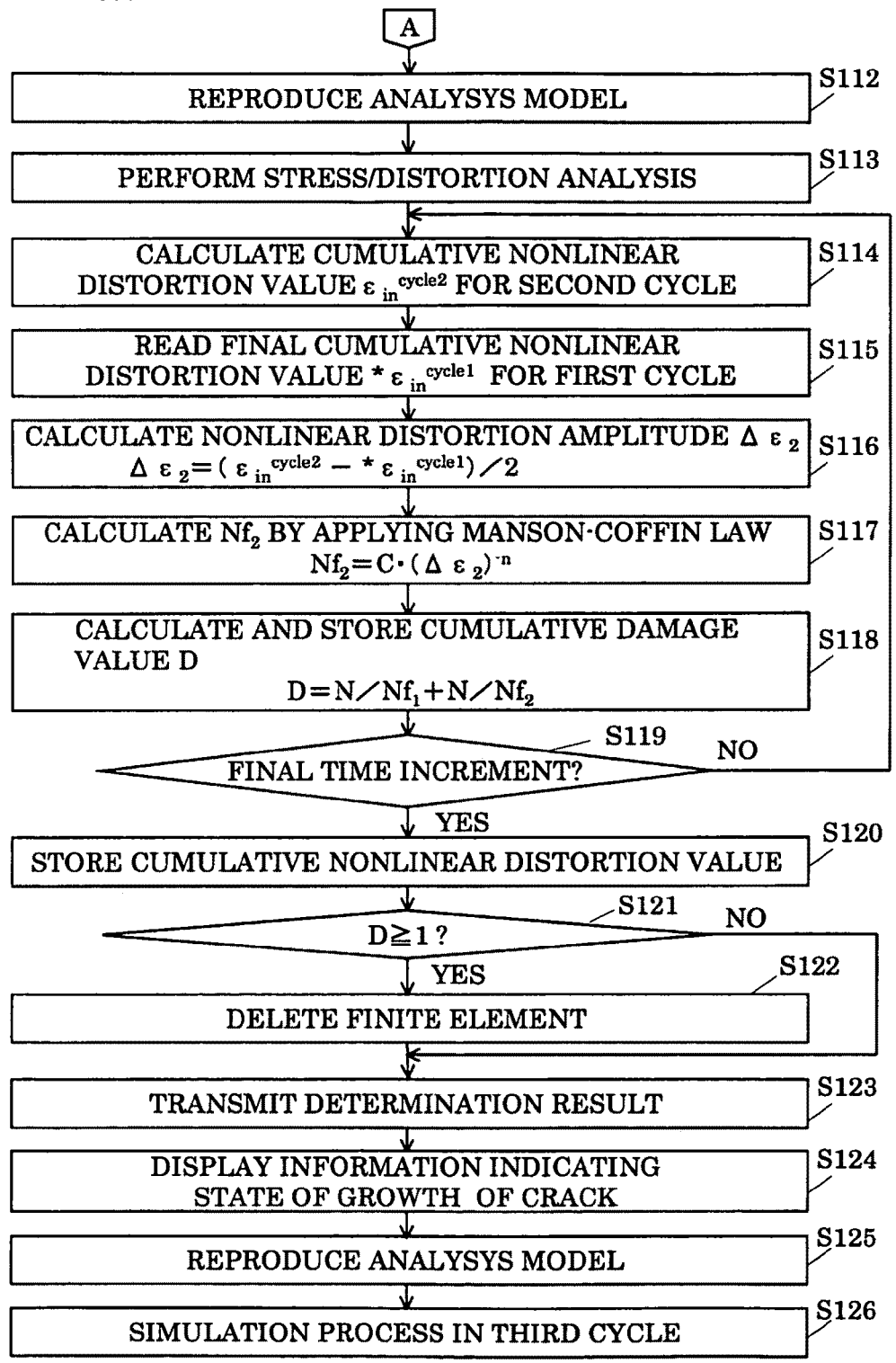

FIGS. 13 and 14 show an example of a flowchart illustrating in detail the simulation process in the step S1 shown in FIG. 8. The example refers to the simulation process performed when the above-mentioned temperature cycle shown in FIG. 2 is applied to a continuum. Steps S101 to S111 shown in FIG. 13 are the steps in the simulation process of the first cycle shown in FIG. 2. Steps S112 to S124 shown in FIG. 14 are the steps in the simulation process of the second cycle shown in FIG. 2. The simulation process in and after the third cycle is similar to the simulation process of the second cycle shown in FIG. 14.

In FIG. 13, the analysis unit 12 performs a stress/distortion analysis on the first cycle for each (all finite elements) of a plurality of finite elements of the continuum (step S101). Next, the determination unit 13 sets a constant N (step S102). After setting the initial value of the cumulative damage value D to 0 (step S103), the processes in the subsequent steps S104 to S111 are performed on each of a plurality of finite elements of the continuum.

That is, the determination unit 13 calculates the cumulative nonlinear distortion value $\epsilon_{in}^{cycle1}$ for the first cycle based on the result of the stress/distortion analysis in the step S101 (step S104). Practically, the determination unit 13 calculates the cumulative nonlinear distortion value $\epsilon_{in}^{cycle1}$ at a point when the process of calculating the damage value is completed for the time increment #4 in the first cycle shown in FIG. 3.

The determination unit 13 calculates a half of the cumulative nonlinear distortion value $\epsilon_{in}^{cycle1}$ as a nonlinear distortion amplitude value $\Delta\epsilon_1$ (step S105), applies the Manson-Coffin law ($Nf_1 = C \cdot (\Delta\epsilon_1)^{-n}$) by the equation 2 to the nonlinear distortion amplitude value $\Delta\epsilon_1$, and calculates the count of cyclic fatigue life $Nf_1$ (step S106). Furthermore, the determination unit 13 calculates the cumulative damage value D by multiplying the value $1/Nf_1$ by a constant N, and stores the cumulative damage value D in the calculation result storage unit 131 (step S107).

The determination unit 13 determines whether or not the process for the final time increment has been completed (step S108). When the process for the final time increment has not been completed, the process in and after the step S104 is repeated. When the process for the final time increment has been completed, the determination unit 13 stores the cumulative nonlinear distortion value as the final cumulative nonlinear distortion value $*\epsilon_{in}^{cycle1}$ for the first cycle (step S109).

Next, the determination unit 13 determines whether or not the cumulative damage value D is equal to or exceeds 1 (step S110). When the determination unit 13 determines that the cumulative damage value D is equal to or exceeds 1, the change unit 14 deletes a finite element having the cumulative damage value D equal to or exceeding 1 (step S111). Afterwards, the generation unit 11 reproduces an analysis model of the continuum (step S112 shown in FIG. 14). When the determination unit 13 determines that the cumulative damage value D is less than 1, the process in the step S112 is performed.

Next, the analysis unit 12 performs a stress/distortion analysis in the second cycle for each of a plurality of finite elements of the continuum (step S113). The determination unit 13 calculates the cumulative nonlinear distortion value $\epsilon_{in}^{cycle2}$ on the second cycle (step S114). Practically, the determination unit 13 calculates the cumulative nonlinear distortion value $\epsilon_{in}^{cycle2}$ when the process of calculating the damage value for the time increment #1 in the second cycle shown in FIG. 3 is completed.

Next, the determination unit 13 reads the final cumulative nonlinear distortion value $*\epsilon_{in}^{cycle1}$ for the first cycle from the calculation result storage unit 131 (step S115), and calculates a half of the difference between $\epsilon_{in}^{cycle2}$ and $\epsilon_{in}^{cycle1}$ as a nonlinear distortion amplitude value $\Delta\epsilon_2$ (step S116). Furthermore, the determination unit 13 applies the Manson-Coffin law ($Nf_2 = C \cdot (\Delta\epsilon_2)^{-n}$) in the equation 2 to the nonlinear distortion amplitude value $\Delta\epsilon_2$ to calculate the count of cyclic fatigue life $Nf_2$ (step S117). Then, the determination unit 13 calculates the cumulative damage value D ($D = N/Nf_1 + N/Nf_2$), and stores the cumulative damage value D in the calculation result storage unit 131 (step S118).

The determination unit 13 determines whether or not the process for the final time increment has been completed (step S119). When the process for the final time increment has not been completed, the process in and after the step S114 is repeated. When the process for the final time increment has been completed, the determination unit 13 stores the cumulative nonlinear distortion value in the calculation result storage unit 131 (step S120).

Next, the determination unit 13 determines whether or not the cumulative damage value D is equal to or exceeds 1 (step S121). When the determination unit 13 determines that the cumulative damage value D is equal to or exceeds 1, the change unit 14 deletes a finite element having the cumulative damage value D equal to or exceeding 1 (step S122). When the determination unit 13 determines the cumulative damage value D is less than 1, the process in the step S123 is performed.

The determination unit 13 transmits a determination result in step S121 (and the cumulative damage value D) to the calculation unit 15 (step S123), and displays the cumulative damage value D of each finite element of the continuum as the information indicating the state of a growth of a crack occurring in the continuum at the end of the second cycle (step S124). Then, the analysis model generation unit 11 reproduces the analysis model of the continuum (step S125). Afterwards, the simulation process in the third cycle is performed (step S126).

In the example of the simulation process described with reference to FIGS. 13 and 14, the display unit 18 displays the information about the state of a growth of a crack occurring in the continuum at the end of the second cycle (refer to step S124 shown in FIG. 14). In another example of the simulation process, the display unit 18 may display the information about the state of a growth of a crack occurring in the continuum at the end of a predetermined cycle.

In addition, in an example of the simulation process described with reference to FIG. 13 and FIG. 14, the determination unit 13 transmits the determination result in the second cycle (and the cumulative damage value D) to the calculation unit 15 (refer to the step 123 shown in FIG. 14). In another example of the simulation process, the determination unit 13 may transmit the determination result in a predetermined cycle to the calculation unit 15.

In the step S111 shown in FIG. 13 and step S122 shown in FIG. 14, the change unit 14 may perform the process of reducing the rigidity of a finite element having the cumulative damage value D equal to or exceeding 1 to a predetermined value instead of the process of deleting the finite element. By the change unit 14 performing the process of reducing the rigidity of the finite element having the cumulative damage value D equal to or exceeding 1 to a predetermined value, for example, the finite element whose rigidity is reduced to the predetermined value in the first cycle is not deleted from the analysis model, but can be a target of the process of calculating the cumulative damage value D in and after the second cycle (refer to the step S118 shown in FIG. 14). Thus, by reducing the rigidity of a finite element to a predetermined value instead of the process of deleting the finite element whose rigidity is reduced to a predetermined value from an analysis model, the necessity to perform the above-mentioned process of reproducing an analysis model of the continuum with reference to the steps S112 and S125 shown in FIG. 14 can be eliminated. Furthermore, since the analysis model is not reproduced, the analyzing process can be practically performed by the analysis unit 12 concurrently with the production of the analysis model. Thus, the processing time can be further shortened.

Figure 15:
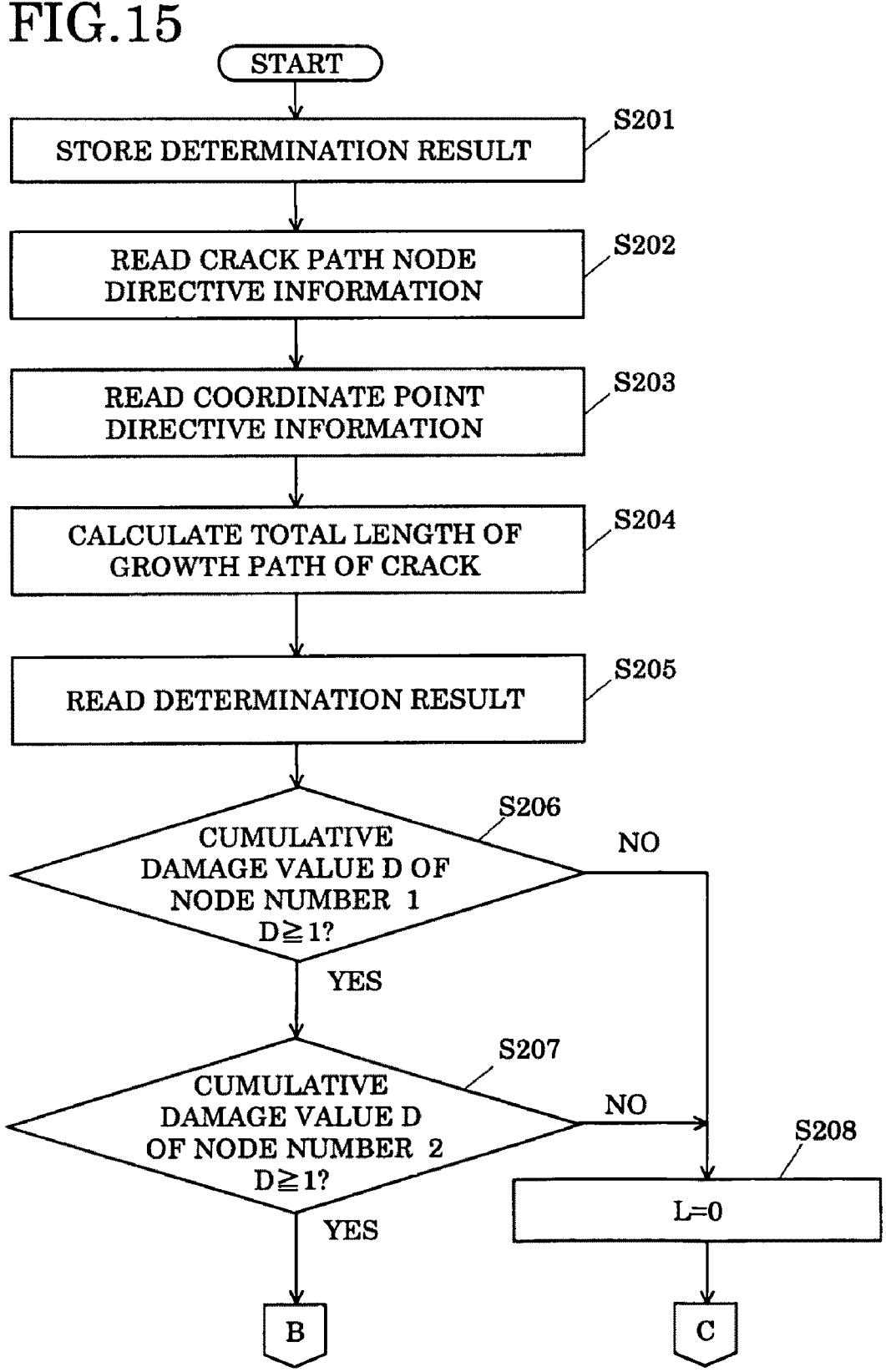
FIGS. 15 and 16 show an example of a flowchart showing the details of the crack growth rate calculating process.
Figure 16:
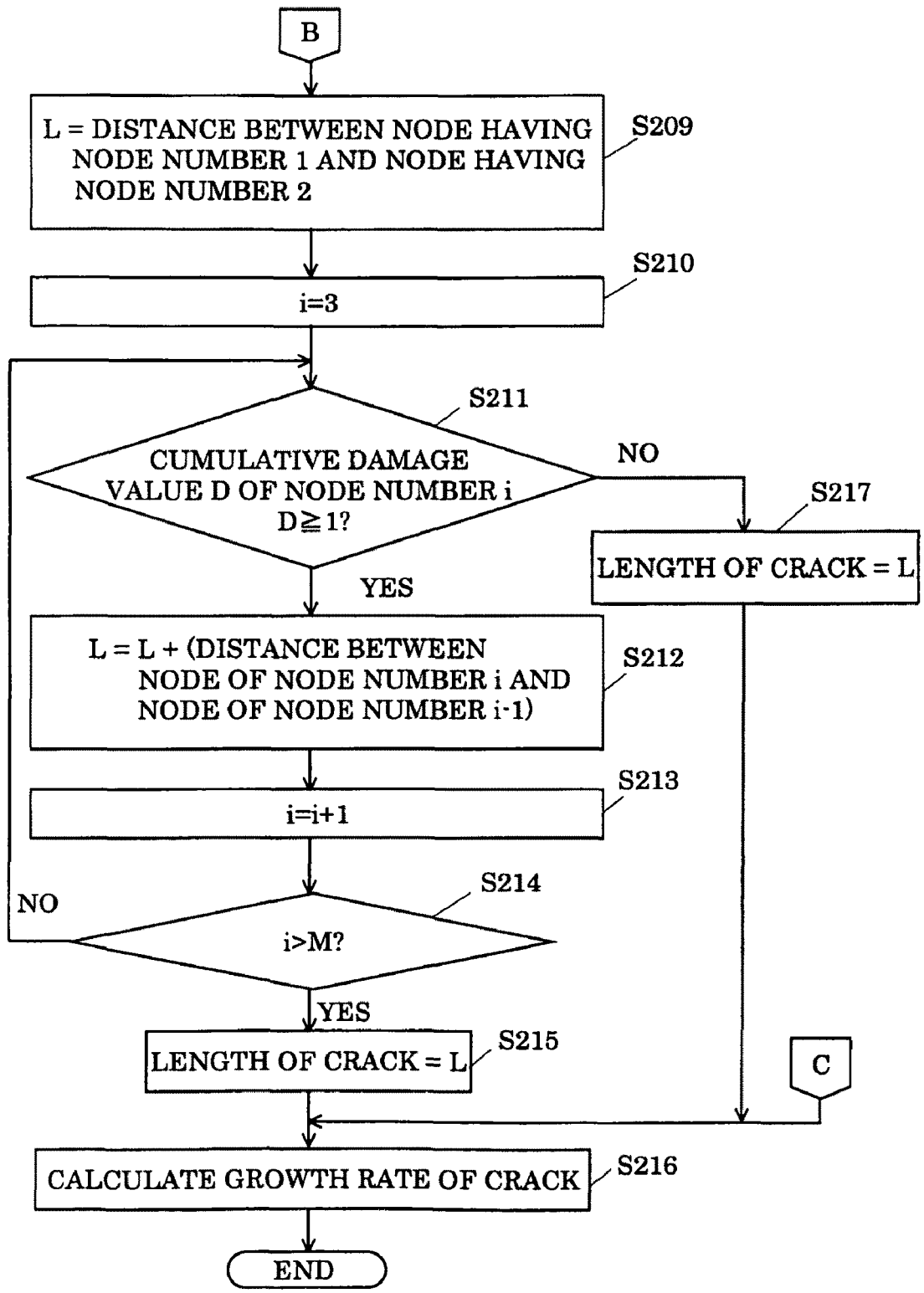

FIGS. 15 and 16 show an example of a flowchart showing the details of the process of calculating a growth rate of a crack in the step S2 shown in FIG. 8 and in the step S13 shown in FIG. 11. In the example, the process of calculating the growth rate of a crack occurring in the soldered portion 102 shown in FIG. 5 is described. "L" shown in FIGS. 15 and 16 indicates a variable showing the length of a crack, "i" shown in FIG. 16 is a variable indicating a node number, and "M" indicates the number of nodes arranged on the growth path of a crack.

The calculation unit 15 stores a determination result as to whether or not the cumulative damage value D transmitted from the determination unit 13 is equal to or exceeds a threshold in the determination result information storage unit 21 (step S201). The calculation unit 15 reads the crack path node directive information corresponding to the continuum as a target of the process of calculating a growth rate of a crack from the crack path node directive information storage unit 19 (step S202), and designates a growth path of a crack occurring in the continuum based on the crack path node directive information. Practically, based on the crack path node directive information, the calculation unit 15 designates that the growth path of a crack of the soldered portion 102 starts from the node P having the node number 1 shown in FIG. 5 and ends at the node S having the node number 4 through the node Q having the node number 2 and the node R of the node number 3.

The calculation unit 15 reads the coordinate point directive information from the coordinate point directive information storage unit 20 (step S203), and obtains the coordinates of a node on the growth path of a crack designated in the step S202 based on the coordinate point directive information. Practically, the calculation unit 15 obtains the coordinates corresponding to the node number 1 of the node P shown in FIG. 5 as the coordinates of the node P based on the coordinate point directive information. Similarly, the calculation unit 15 obtains the coordinates of the node Q, the coordinates of the node R, and the coordinates of the node S shown in FIG. 5.

The calculation unit 15 calculates the total length of the growth path of a crack based on the coordinates of the node on the growth path of a crack obtained in the step S203 (step S204). Practically, the calculation unit 15 calculates a total of the distance between the node P and the node Q, the distance between the node Q and the node R, and the distance between the node R and the node S shown in FIG. 5 as the total length of the growth path of a crack of the soldered portion 102 shown in FIG. 5.

Next, the calculation unit 15 reads a determination result from the determination result information storage unit 21 (step S205). Practically, the calculation unit 15 reads from the determination result information storage unit 21 the determination result corresponding to the node P having the node number 1, the determination result corresponding to the node Q having the node number 2, the determination result corresponding to the node R having the node number 3, and the determination result corresponding to the node S having the node number 4 shown in FIG. 5.

Next, the calculation unit 15 determines whether or not the cumulative damage value D of the finite element corresponding to the node number 1 is equal to or exceeds 1 based on the determination result corresponding to the node number 1 (step S206). When the cumulative damage value D of the finite element corresponding to the node number 1 is less than 1, the calculation unit 15 sets the length of the crack to 0 (L=0), and performs the process in step S216 shown in FIG. 16 (step S208).

When the cumulative damage value D of the finite element corresponding to the node number 1 is equal to or exceeds 1, the calculation unit 15 determines whether or not the cumulative damage value D of the finite element corresponding to the node number 2 is equal to or exceeds 1 based on the determination result corresponding to the node number 2 (step S207). When the cumulative damage value D of the finite element corresponding to the node number 2 is less than 1, the calculation unit 15 performs the process in the step S208, and then performs the process in the step S216 shown in FIG. 16.

When the cumulative damage value D of the finite element corresponding to the node number 2 is equal to or exceeds 1, the calculation unit 15 calculates the distance between the node having the node number 1 and the node having the node number 2, and sets the value of the calculated distance as the length L of the crack (step S209). Afterwards, the calculation unit 15 sets the node number to 3 (i=3) (step S210), and determines whether or not the cumulative damage value D of the finite element corresponding to the node number i is equal to or exceeds 1 (step S211).

When the cumulative damage value D of the finite element corresponding to the node number i is less than 1, the calculation unit 15 defines the value set as L as the length of the crack (step S217). Afterwards, the calculation unit 15 performs the process in step S216.

When the cumulative damage value D of the finite element corresponding to the node number i is equal to or exceeds 1, the calculation unit 15 calculates the distance between the node having the node number i and the node having the node number i-1, and the sum of the calculated value and the value L is set as the value L (step S212). Afterwards, the calculation unit 15 increments the node number by 1 (i=i+1) (step S213), and determines whether or not i exceeds M (i>M) (step S214). Practically, since the number of the nodes on the growth path of a crack of the soldered portion 102 shown in FIG. 5 is four, the calculation unit 15 determines whether or not i is larger than 4. When i is equal to or less than M, the processes in and after step S211 are repeated.

When i is larger than M (i>M), the calculation unit 15 defines the value set as L as the length of a crack (step S215). Afterwards, the calculation unit 15 divides the value of L by the total length of the growth path of a crack calculated in the step S204 shown in FIG. 15, and calculates the growth rate of a crack (step S216). Practically, the calculation unit 15 calculates the growth rate of a crack by the following equation.

Growth rate of a crack=(value of L/total length of growth path of a crack)×100(%)

Next, a result of a practical simulation performed on the soldered portion of electronic parts by the crack growth evaluation apparatus 1 according to the present embodiment is described below with reference to FIGS. 17 to 25.

In this example, the crack growth evaluation apparatus 1 performs a simulation process on the soldered portion of a BGA (ball grid array) package. In the simulation process, the crack growth evaluation apparatus 1 sets, for example, a predetermined value (number of cycles) to 100, performs the simulation process on the temperature cycle for 15 cycles, and evaluates the growth of a crack when 1500 temperature cycles are applied to the soldered portion.

FIG. 17 is a diagram showing an analysis model of a BGA package generated by the crack growth evaluation apparatus 1 in the simulation process. The generation unit 11 of the crack growth evaluation apparatus 1 generates an analysis model including an electronic part (semiconductor chip) 100, a packaging substrate 101, and the soldered portion 102 shown in FIG. 17. Practically, FIG. 17 shows a screen for display by the display unit 18. In FIG. 17, the right end portion of the screen shows a bar in each color depending on the number so that a finite element of the analysis model is displayed in each color (the same holds true in FIG. 18).

FIG. 18 is a diagram showing a partially expanded portion of the analysis model of a BGA package shown in FIG. 17. In the simulation process, the crack growth evaluation apparatus 1 performs the crack growth evaluating process on the crack occurring in the soldered portion 102 using eutectic solder of SnPb which is a solder material of the soldered portion 102 as a continuum.

The soldered portion 102 in the analysis model shown in FIG. 18 is further expanded to be equal to FIG. 25. That is, FIG. 25 is a partially enlarged analysis model of a BGA package shown in FIG. 18. FIGS. 20 to 23 corresponds to FIG. 25, and shows a result of the simulation process (crack growth evaluation) according to the present embodiment on the analysis model.

FIG. 19 is a diagram showing the temperature cycle applied to a soldered portion. In 1 cycle of the temperature cycle, the soldered portion 102 is held at −40° C. for about 30 minutes, and then held at 125° C. for about 30 minutes. Practically, one cycle time is about 1.16 hour. The crack growth evaluation apparatus 1 performs the crack growth evaluating process using the temperature condition shown in FIG. 19 as load information to be applied to the soldered portion 102.

FIGS. 20, 21, 22, and 23 are diagrams showing a result of the simulation process according to the present embodiment. Practically, FIGS. 20, 21, 22, and 23 show screens for display by the display unit 18. In FIGS. 20 to 23, the right end portion of the screen shows a bar in each color depending on the number of finite element to display the size of the cumulative damage value D of the finite element of the soldered portion 102 in each color.

In the bar, a diagonally shaded area indicates that the cumulative damage value D is equal to or exceeds a predetermined threshold. In the soldered portion 102 shown in FIG. 20, the area provided with the same diagonal lines as the diagonally shaded area in the bar is an area including a finite element having the cumulative damage value D equal to or exceeds the predetermined threshold. Therefore, the diagonally shaded area in the soldered portion 102 refers to the portion where a crack has occurred (grown).

FIGS. 20, 21, 22, and 23 show a state of the growth of a crack of a finite element of the soldered portion 102 respectively at a 200 cycle end point, a 500 cycle end point, a 700 cycle end point, and a 900 cycle end point. With reference to FIGS. 20 to 23, with an increasing number of temperature cycles to be applied to the soldered portion 102, the crack is expands (grows).

FIG. 24 is a diagram showing an example of displaying the length of a crack occurring in the soldered portion for each predetermined number of cycles calculated by the crack growth evaluation apparatus in the simulation process of the present embodiment. In the example, the display of the length of the crack calculated by the crack growth evaluation apparatus 1 of the present embodiment based on a result of the simulation process using a new Manson-Coffin law (refer to the step S13 shown in FIG. 11, and the step S215 shown in FIG. 16) is described.

In FIG. 24, a graph 200 shows the length of a crack calculated by the crack growth evaluation apparatus 1 of the present embodiment, and a graph 201 shows the actual measurement value of the length of a crack. With reference to FIG. 24, the crack growth evaluation apparatus 1 of the present embodiment correctly performs a simulation of a state of a growth of a crack.

According to the crack growth evaluation apparatus and the crack growth evaluation method of the present embodiment, a simulation is performed using a Manson-Coffin law changed based on an actual measurement result in the growth process of a crack occurring in a continuum, thereby obtaining a simulation result with high accuracy on the growth process of a crack. As a result, the growth of a crack occurring in a continuum can be evaluated with high accuracy.

In addition, for example, when the crack growth evaluation apparatus of the present embodiment deletes a finite element having a cumulative value of a damage value of the continuum equal to or exceeding a threshold, the deleted finite element falls out of a target of a stress/distortion analysis in the next cycle. As a result, the process of evaluating a growth of a crack occurring in a continuum can be performed without suspension in midstream. Furthermore, for example, when the crack growth evaluation apparatus of the present embodiment changes the rigidity of the finite element, the state of a growth of a crack occurring in a continuum can be evaluated without reproducing an analysis model.

Additionally, according to the crack growth evaluation apparatus of the present embodiment, a growth rate of a crack occurring in a continuum can be automatically calculated based on the information about a node of a finite element arranged on a growth path of a crack occurring in a continuum and a comparison result between the cumulative value of the damage value of a finite element and the threshold. In addition, according to the crack growth evaluation apparatus based on the present embodiment, for example, a designer of a continuum can appropriately change the shape of a continuum based on the calculated growth rate of a crack, thereby designing a long-life continuum with stability without unevenness.

Furthermore, according to the crack growth evaluation apparatus of the present embodiment, a state of a growth of a crack occurring in a continuum can be automatically displayed with high accuracy.

What is claimed is:

1. A crack growth evaluation apparatus with a processor that evaluates a growth of a crack occurring in a continuum, comprising:
   a generation unit running on the processor and generating an analysis model used in analyzing stress and distortion occurring in the continuum by a finite element method and obtained by dividing the continuum into a plurality of finite elements;
   an analysis unit running on the processor and analyzing, by the finite element method, a stress and a distortion occurring by a load cyclically applied to the continuum in each of a plurality of finite elements of the continuum for each cycle of the load using the analysis model;
   a determination unit running on the processor and calculating a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold;
   a calculation unit running on the processor and calculating a growth rate of a crack occurring in the continuum when the cycle of the load terminates for each cycle of the load based on the determination result by the determination unit, and obtaining first correspondence information indicating a correspondence between the number of cycles of a load and the growth rate of a crack;

a Manson-Coffin law change unit running on the processor and changing the Manson-Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum; and a change unit running on the processor and deleting a finite element having a cumulative value of the damage value equal to or exceeding the threshold when the cumulative value is equal to or exceeds the threshold, or changing rigidity of the finite element, wherein the analysis unit analyzes stress and distortion occurring by a load of a next cycle after a current cycle for each of a plurality of finite elements of the continuum whose finite element is deleted or whose rigidity is changed by the change unit when the current cycle of the load cycle terminates, wherein the calculation unit sets a node arranged at a starting position of the growth path of the crack where the cumulative value is equal to or exceeds the threshold as the node where a crack starts using extrapolated information stored in advance in a storage unit, calculates a path length from the node where a crack starts to a last node where the cumulative value is equal to or exceeds the threshold as a length of the crack occurring in the continuum, and calculates a rate of the calculated crack length to a total length of the growth path of a crack as a growth rate of a crack occurring in the continuum, and wherein the Manson-Coffin law change unit obtains an actual measurement value of the number of cycles of a load when the growth rate of a crack calculated by the calculation unit and the number of cycles of a load corresponding to the growth rate of a crack respectively match an actual measurement value of the growth rate of a crack and an actual measurement value of the number of cycles of a load corresponding to the actual measurement value of the growth rate of a crack, calculates a plurality of nonlinear distortion amplitude values each corresponding to the obtained actual measurement value of the number of cycles of a load, and obtains a new Manson-Coffin law by least square approximation using a plurality of sets of the calculated nonlinear distortion amplitude values and the obtained actual measurement value of the number of cycles of a load corresponding with each other.

2. The crack growth evaluation apparatus according to claim 1, wherein the determination unit subtracts the cumulative nonlinear distortion value in the preceding cycle to the current cycle from the cumulative nonlinear distortion value in the current cycle of the load cycle for each of a plurality of finite elements of the continuum to calculate the nonlinear distortion amplitude value in the current cycle.

3. The crack growth evaluation apparatus according to claim 1, further comprises a display unit displaying a state of a growth of a crack occurring in the continuum using the analysis model based on a determination result by the determination unit.

4. The crack growth evaluation apparatus according to claim 3, wherein the display unit displays the first correspondence information obtained by the calculation unit.

5. The crack growth evaluation apparatus according to claim 1, wherein the continuum includes a soldered portion of electronic parts.

6. A crack growth evaluation method for evaluating a growth of a crack occurring in a continuum by using a computer processor, comprising:

generating, in a generation unit running on the computer processor, an analysis model used in analyzing stress and distortion occurring in the continuum by a finite element method and obtained by dividing the continuum into a plurality of finite elements;

analyzing, in an analysis unit running on the computer processor, by the finite element method, a stress and the distortion occurring by a load cyclically applied to the continuum in each of a plurality of finite elements of the continuum for each cycle of the load using the analysis model;

calculating, in a calculation and determination unit running on the computer processor, a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold;

calculating, in a calculation unit running on the computer processor, a growth rate of a crack occurring in the continuum when the cycle of the load terminates for each cycle of the load based on the determination result, and obtaining first correspondence information indicating a correspondence between the number of cycles of a load and the growth rate of a crack;

changing, in a change unit running on the computer processor the Manson-Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum; and deleting, in a deletion unit running on the computer processor, a finite element having a cumulative value of the damage value equal to or exceeding the threshold when the cumulative value is equal to or exceeds the threshold, or changing rigidity of the finite element, wherein the analyzing analyzes stress and distortion occurring by a load of a next cycle after a current cycle for each of a plurality of finite elements of the continuum whose finite element is deleted or whose rigidity is changed by the change unit when the current cycle of the load cycle terminates, wherein the calculation unit sets a node arranged at a starting position of the growth path of the crack where the cumulative value is equal to or exceeds the threshold as the node where a crack starts using extrapolated information stored in advance in a storage unit, calculates a path length from the node where a crack starts to a last node where the cumulative value is equal to or exceeds the threshold as a length of the crack occurring in the continuum, and calculates a rate of the calculated crack length to a total length of the growth path of a crack as a growth rate of a crack occurring in the continuum, and wherein the change unit obtains an actual measurement value of the number of cycles of a load when the growth rate of a crack calculated by the calculation unit and the number of cycles of a load corresponding to the growth rate of a crack respectively match an actual measurement value of the growth rate of a crack and an actual measurement value of the number of cycles of a load corresponding to the actual measurement value of the growth rate of a crack, calculates a plurality of nonlinear distortion amplitude values each corresponding to the obtained actual measurement value of the number of cycles of a load, and obtains a new Manson-Coffin law by least square approximation using a plurality of sets of the calculated nonlinear distortion amplitude values and the obtained actual measurement value of the number of cycles of a load corresponding with each other.

7. A non-transitory computer-readable medium containing instructions stored therein for causing a computer processor to perform:

generating an analysis model used in analyzing stress and distortion occurring in the continuum by a finite element method and obtained by dividing the continuum into a plurality of finite elements;

analyzing, by the finite element method, a stress and the distortion occurring by a load cyclically applied to the continuum in each of a plurality of finite elements of the continuum for each cycle of the load using the analysis model;

calculating a cumulative nonlinear distortion value for each of the plurality of finite elements of the continuum for each cycle of the load cyclically applied to the continuum using the analysis model based on the analysis result, calculating a nonlinear distortion amplitude value based on the calculated cumulative nonlinear distortion value, calculating a damage value using a Manson-Coffin law based on the calculated nonlinear distortion amplitude value, calculating a cumulative value based on the calculated damage value, comparing the cumulative value with a predetermined threshold, and determining whether or not the cumulative value is equal to or exceeds the threshold;

calculating a growth rate of a crack occurring in the continuum when the cycle of the load terminates for each cycle of the load based on the determination result, and obtaining first correspondence information indicating a correspondence between the number of cycles of a load and the growth rate of a crack;

changing the Manson-Coffin law based on the first correspondence information and second correspondence information indicating a correspondence between an actual measurement value of the number of cycles of a load cyclically applied to the continuum and an actual measurement value of the growth rate of a crack occurring in the continuum when the load is applied for the number of cycles to the continuum; and deleting a finite element having a cumulative value of the damage value equal to or exceeding the threshold when the cumulative value is equal to or exceeds the threshold, or changing rigidity of the finite element, wherein the analyzing analyzes stress and distortion occurring by a load of a next cycle after a current cycle for each of a plurality of finite elements of the continuum whose finite element is deleted or whose rigidity is changed by the change unit when the current cycle of the load cycle terminates, wherein said calculating a growth rate of a crack includes setting a node arranged at a starting position of the growth path of the crack where the cumulative value is equal to or exceeds the threshold as the node where a crack starts using extrapolated information stored in advance in a storage unit, calculating a path length from the node where a crack starts to a last node where the cumulative value is equal to or exceeds the threshold as a length of the crack occurring in the continuum, and calculating a rate of the calculating crack length to a total length of the growth path of a crack as a growth rate of a crack occurring in the continuum, and wherein said changing includes obtaining an actual measurement value of the number of cycles of a load when the growth rate of a crack calculated by said calculating a growth rate of a crack unit and the number of cycles of a load corresponding to the growth rate of a crack respectively match an actual measurement value of the growth rate of a crack and an actual measurement value of the number of cycles of a load corresponding to the actual measurement value of the growth rate of a crack, calculating a plurality of nonlinear distortion amplitude values each corresponding to the obtained actual measurement value of the number of cycles of a load, and obtaining a new Manson-Coffin law by least square approximation using a plurality of sets of the calculated nonlinear distortion amplitude values and the obtained actual measurement value of the number of cycles of a load corresponding with each other.

8. A crack growth evaluation apparatus with a processor that evaluates a growth of a crack occurring in a continuum, comprising:

a simulation unit running on the processor and performing a simulation process using a Manson-Coffin law;

a calculation unit running on the processor and calculating a growth rate of a crack based on the simulation process and to obtain first correspondence information indicating a correspondence between a number of cycles of a load and the growth rate of the crack;

an actual measurement value input unit running on the processor and inputting second correspondence information indicating a correspondence between an actual measurement value of the number of cycles of the load and an actual measurement value of the growth rate of the crack; and a Manson-Coffin law change unit running on the processor and calculating the actual measurement value of the number of cycles of the load when the simulation value of the growth rate of the crack obtained by the calculation unit and the simulation value of the number of cycles of the load respectively match the actual measurement value of the growth rate of the crack input by the actual measurement value input unit and the actual measurement value of the number of cycles of the load correspond to the actual measurement value of the growth rate of the crack;

the Manson-Coffin law change unit calculating nonlinear distortion amplitude values corresponding to the actual measurement values of the number of cycles of the load;

the Manson-Coffin law change unit obtaining a new Manson-Coffin law using least square approximation based on the correspondence information between the actual measurement values of the number of cycles of the load and the nonlinear distortion amplitude values obtained.

* * * * *